United States Patent [19]

Oyama et al.

[11] Patent Number: 4,816,118
[45] Date of Patent: Mar. 28, 1989

[54] ION-SENSITIVE FET SENSOR

[75] Inventors: Noboru Oyama, Fuchu; Takeshi Shimomura, Fujinomiya; Shuichiro Yamaguchi, Fuji, all of Japan

[73] Assignee: Terumo Corporation, Tokyo, Japan

[21] Appl. No.: 203,504

[22] Filed: Jun. 2, 1988

Related U.S. Application Data

[63] Continuation of Ser. No. 875,061, Jun. 17, 1986, abandoned.

[30] Foreign Application Priority Data

Jan. 24, 1986 [JP] Japan .................... 61-13486
Feb. 14, 1986 [JP] Japan .................... 61-30394

[51] Int. Cl.$^4$ ............................................. G01N 27/30
[52] U.S. Cl. .................................... 204/418; 204/416; 357/25
[58] Field of Search ................. 204/416, 418, 419; 357/25; 128/635

[56] References Cited

U.S. PATENT DOCUMENTS

| | | | |
|---|---|---|---|
| 3,926,764 | 12/1975 | Ruzicka et al. | 204/195 |
| 3,932,233 | 1/1976 | Ruzicka et al. | 204/1 T X |
| 3,957,612 | 5/1976 | Niedrach et al. | 204/195 |
| 3,957,613 | 5/1976 | Macur | 204/195 |
| 4,052,285 | 10/1977 | Dobson | 204/195 |
| 4,115,209 | 9/1978 | Freiser et al. | 204/1 T |
| 4,198,851 | 4/1980 | Janata | 73/23 |
| 4,214,968 | 7/1980 | Battaglia et al. | 204/195 |
| 4,280,889 | 7/1981 | Szonntagh | 204/195 |
| 4,282,099 | 8/1981 | Chang et al. | 204/420 |
| 4,305,802 | 12/1981 | Koshiishi | 357/25 X |
| 4,454,007 | 6/1984 | Pace | 204/1 T |
| 4,512,870 | 4/1985 | Kohara et al. | 204/416 |
| 4,549,951 | 10/1985 | Knudson et al. | 204/416 |
| 4,561,962 | 12/1985 | Kankare | 204/415 |
| 4,563,263 | 1/1986 | Oyama et al. | 204/418 |
| 4,615,954 | 10/1986 | Solomon et al. | 429/27 |
| 4,632,732 | 12/1986 | Fog et al. | 204/1 T |

FOREIGN PATENT DOCUMENTS

| | | | |
|---|---|---|---|
| 56283 | 7/1982 | European Pat. Off. | |
| 01186210 | 7/1986 | European Pat. Off. | 204/418 |
| 0186210 | 7/1986 | European Pat. Off. | |
| 3134760 | 9/1982 | Fed. Rep. of Germany | 204/416 |
| 52-30490 | 8/1977 | Japan | 204/431 |
| 57-6344 | 4/1982 | Japan | 204/418 |
| 57-196116 | 12/1982 | Japan | 204/416 |
| 58-167951 | 10/1983 | Japan | |
| 59-57156 | 4/1984 | Japan | 204/418 |
| 59-164952 | 9/1984 | Japan | 204/416 |
| 60-7357 | 1/1985 | Japan | 204/418 |
| 60-52759 | 3/1985 | Japan | 204/416 |
| 60-73351 | 4/1985 | Japan | 204/416 |
| 898314 | 1/1982 | U.S.S.R. | |

OTHER PUBLICATIONS

Tamura et al., "Coated Wire Sodium- and Potassium-Electrodes Based on Bis(crown ether) Compounds", Analytical Chemistry, vol. 54, No. 7, Jun. 1982, pp. 1224–1227.

Wuthier et al., "Tin Organic Compounds as Neutral Carriers for Anion Selective Electrodes", Analytical Chemistry, vol. 56, No. 3, Mar. 1984, pp. 535–538.

Norov et al., "Calcium-Selective Electrode Without an Internal Reference Solution", Journal of Analytical Chemistry, vol. 34, No. 8, Part 1, Aug. 1979, pp. 1159–1162.

(List continued on next page.)

Primary Examiner—G. L. Kaplan
Attorney, Agent, or Firm—Burns, Doane, Swecker & Mathis

[57] ABSTRACT

An ion-sensitive FET sensor has a MOSFET gate isolating membrane whose surface is covered by an ion-sensitive layer. A redox layer having a redox function is provided between the isolating membrane and the ion-sensitive layer to improve operating stability and speed of response. An electrically conductive layer or a combination of a thin metal film and an electrically conductive layer is provided between the isolating membrane and the redox layer to further improve operating stability, the adhesion of the layers and the durability of the sensor. Also disclosed are optimum materials for use as an ion carrier employed in the ion-sensitive layer.

59 Claims, 14 Drawing Sheets

OTHER PUBLICATIONS

Oyama et al., "Hydrogen Ion Selective Microelectrode Prepared By Modifying An Electrode With Polymers", Analytical Chemistry 1987, vol. 59, pp. 258–262.

Oyama, "Ion Selective Microelectrode Prepared By Modifying An Electrode With Polymers", International Electrical Symposium, Schaumberg, Illinois, May 27–29 (1987), pp. 122–125.

Oyama et al., "A New Type of Ion-Selective Microelectrodes Using Electropolymerize Thin Films", j-4 Bioelectroanalytical Chemistry Symposium, Honolulu, Hawaii, Oct. 18–23, 1987.

Oyama et al., "Ion Selective Electrode Prepared By Modifying an Electrode With Polymers", Tokyo Seminar on Macromolecular Complexes, Tokyo Univ., Oct. 14–17, 1987.

Moss et al., "Potassium Ion-Sensitive Field Effect Transistor," Analytical Chemistry, vol. 47, No. 13, Nov. 1975.

Cattrall et al., "Potassium Ion Responsive Coated Wire Electrode Based on Valinomycin," Analytical Chemistry, vol. 46, No. 14, Dec. 1974.

Ohnuki et al., "Permselectivity of Films Prepared by Electrochemical Oxidation of Phenol and Amino-Aromatic Compounds," J. Electroanal. Chem., 158 (1983) 55–67.

Heinemann et al., "Polymer Film Chemically Modified Electrode as a Potentiometric Sensor," Anal. Chem. 1980, 52, 345–346.

Cheek et al., "pH Response of Platinum and Vitreous Carbon Electrodes Modified by Electropolymerized Films," Anal. Chem. 1983, 55, 380–381.

Rubinstein, "Voltammetric pH measurements with Surface-Modified Electrodes and a Voltammetric Internal Reference," Anal. Chem. 1984, 56, 1135–1137.

Oyama et al., "Facile Attachment of Transition Metal Complexes to Graphite Electrodes Coated With Polymeric Ligands, Observation and Control of Metal-Ligand Coordination among Reactants Confined to Electrode Surfaces," Journal of the American Chemical Society, 101, 739 (1979).

Oyama et al., "Electrostatic Binding of Metal Complexes to Electrode Surfaces Coated with Highly Charged Polymeric Films," J. Electrochem. Soc., vol. 127, No. 1, Jan. 1980, pp. 247–250.

Oyama et al., "Catalysis of Electrode Processes by Multiply-Charged Metal Complexes Electrostatically Bound to Polyelectrolyte Coatings on Graphite Electrodes, and the Use of Polymer-Coated Rotating Disk Electrodes in Diagnosing Kinetic and Conduction Mechanisms," Anal. Chem. 1980, 52, 1192–1198.

Snell et al., "Surface Modified Electrodes," Chem. Soc. Rev. 1979, 8, 259–282.

Faulkner, "Chemical Microstructures on Electrodes," Chem. Eng. News, 1984, 27, pp. 28–45.

Oyama et al., "Electrochemical Properties of Electropolymerized Poly (1-pyrenamine) Films," Bull. Chem. Soc. Jpn., 1986, 59, 2071–2080.

Schulthess et al., "A Hydrogen-Ion Selective Liquid-Membrane Electrode based on Tri-n-Dodecylamine as Neutral Carrier," Analytica Chimica Acta, 131, (1981) 111–116.

Electrochemical Detectors Fundamental Aspects and Analytical Applications, T. H. Ryan, p. 7.

Organic Analysis Using Ion-Selective Electrodes, vol. 2, T. S. Ma, pp. 60 and 62.

Oyama et al., "Electrochemical Properties of Electropolymerized Poly (1-pyrenamine) Films," The Chemical Society of Japan, Jul. 1986.

T. H. Ryan, "Electrochemical Detectors", p. 7.

Ma et al., "Oranic Analysis Using Ion-Sensitive Electrodes", vol. 2, pp. 60 & 62.

Ammann, "Ion-Selective Microelectrodes", Principles, Design & Application, pp. 5–7, 66 & 100.

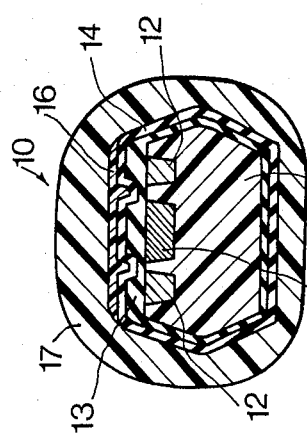
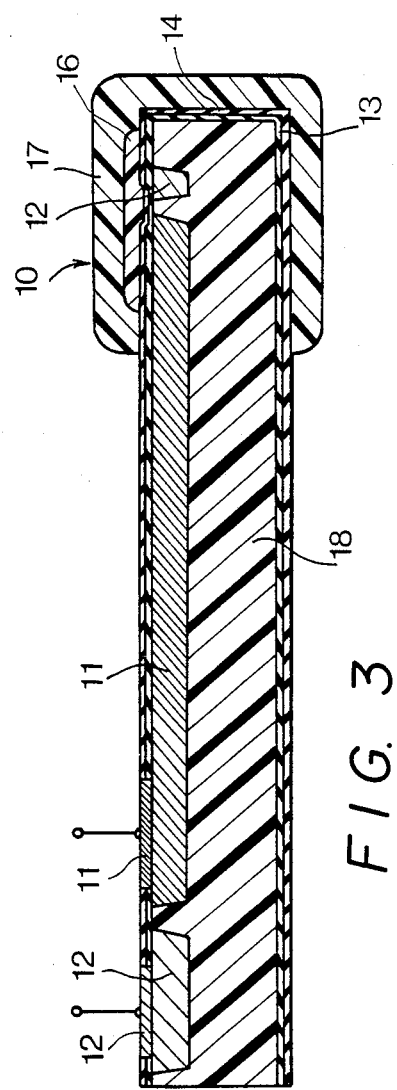
FIG. 2
FIG. 3

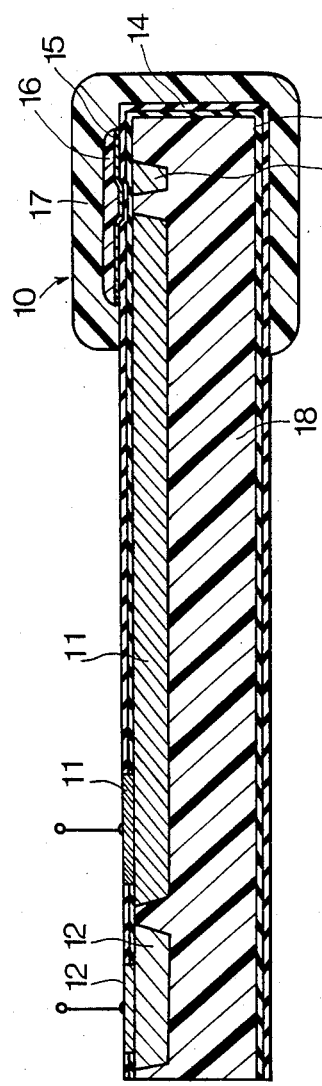
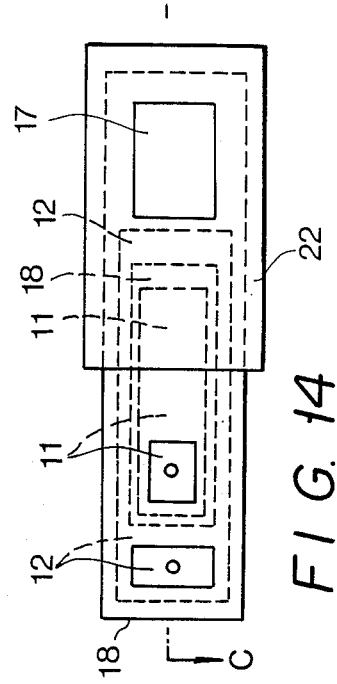
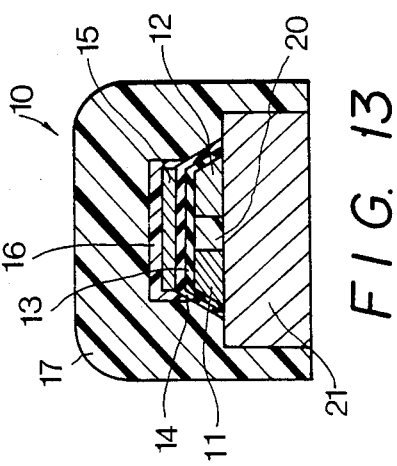

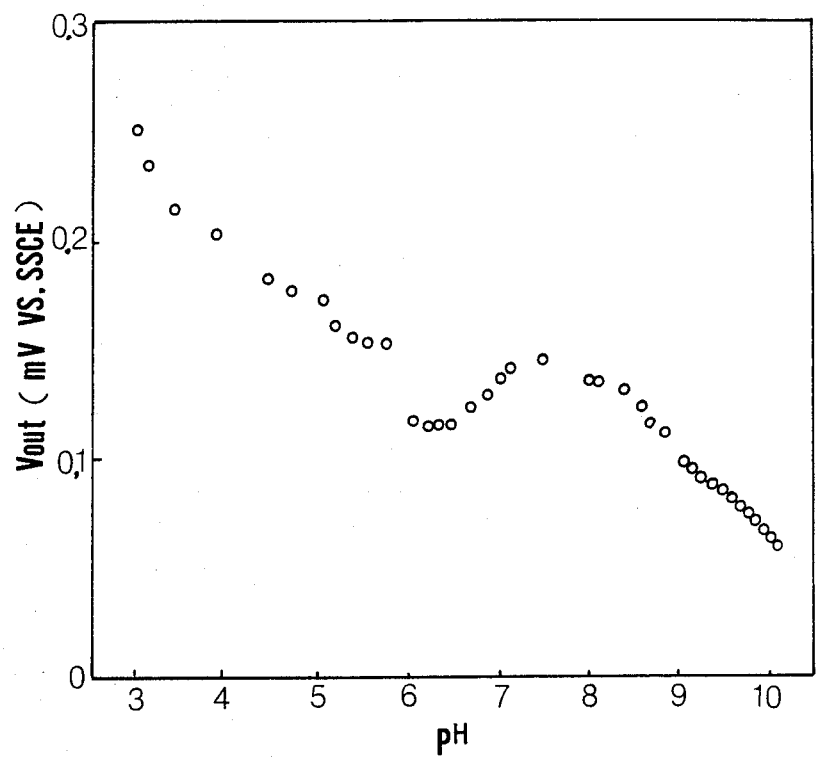
F I G. 18

ION-SENSITIVE FET SENSOR

This application is a continuation of application Ser. No. 875,061, filed June 17, 1986 now abandoned.

BACKGROUND OF THE INVENTION (1) Field of the Invention

This invention relates to an ion-sensitive FET sensor and, more particularly, to an ion-sensitive FET (hereafter referred to as an "ISFET") sensor for measuring the ionic concentration of a solution by the potentiometric response of an electrode. The ISFET sensor disclosed herein is especially suited for measurement of ionic concentration within a living body.

(2) Description of the Prior Art

A variety of chemical semiconductor instruments comprising a chemical sensor and a semiconductor device in integrated form have been developed in recent years. One example is the aforementioned ISFET, which is an integrated combination of of a MOS-type field-effect transistor (MOSFET) and an ion-sensitive electrode. The ISFET is a sensor of a novel type radically different from the ion sensors of old and can be made very small in size, exhibits such excellent characteristics as the high input impedance and low noise of the MOSFET, and has a very short response time. Owing to these outstanding sensor features, the ISFET has attracted much attention.

However, the ISFETs investigated so far basically have been adapted for use as pH sensors, and only recently have sensors for measurement of ion concentrations other than hydrogen ion begun to be studied. The structure of an ion-sensitive layer is of prime importance for obtaining an ISFET having excellent sensor characteristics. Problems are encountered in terms of the adherability and water-resistant property of the ion-sensitive layer, and all ion sensors generally share the significant drawback of potential drift. Potential is unstable, characteristics deteriorate due to the adsorption of proteins and the like, and clotting tends to occur when measurement is made in a blood sample.

It is known from, e.g. the specification of Japanese Patent Application Laid-Open No. 59-164952, that potential drift can be reduced by adopting a structure in which a polymeric membrane layer devoid of an ion-sensitive substance is interposed between a gate isolating layer and an ion-sensitive layer for the purpose of improving the adhesion between these two layers. However, as a result of the poor electronic conductivity of the intervening polymeric membrane layer, an ion sensor having such a structure exhibits a high membrane impedance and is susceptible to noise and other disturbances when a measurement is made.

It is known from, e.g. the specifications of Japanese Patent Application Laid-Open Nos. 57-63444, 60-73351, that a highly durable ion sensor having an ion-sensitive layer of improved adherability is obtained by adopting a structure in which a metallic membrane is interposed between the gate isolating layer and the ion-sensitive layer. However, the problem with such an expedient is poor stability ascribed to the fact that the gate portion of the sensor is readily influenced by oxygen.

Accordingly, there is demand for an ion sensor having good adhesion between the ion-sensitive layer and the gate portion, outstanding durability and excellent stability with little susceptibility to the effects of interfering ions.

As for ion sensors for measurement of pH, the few known use $SiO_2$, $SiN_4$, $Al_2O_3$ or $Ta_2O_5$ as a hydrogen ion-sensitive layer. Moreover, the ion sensor that relies upon $Si_2O_3$ as the hydrogen ion-sensitive layer generally exhibits unstable operation and has little utility value. Ideal hydrogen ion-sensitive layers for pH measurement ISFETs exhibiting good pH response and little interference from other ions such as alkali metal ions are limited to membranes consisting of chemically stable compounds such as $Al_2O_3$ and $Ta_2O_5$.

SUMMARY OF THE INVENTION

Accordingly, the inventor has performed exhaustive research in an effort to eliminate the aforementioned defects of the ion-sensitive layer constituting an ISFET. As a result of this research, the inventor has found that an ISFET sensor having excellent adherability and water resistance and exhibiting outstanding sensor characteristics can be obtained if the sensor includes (a) a redox layer and (b) a polymeric membrane serving as the ion-sensitive layer, the membrane containing an ion carrier substance for the specific ion of interest. The invention has been perfected on the basis of this discovery.

More specifically, the present invention provides an ion-sensitive FET sensor characterized by comprising a MOSFET, a layer having a redox function deposited on the gate isolating layer of the MOSFET, and an ion-sensitive layer deposited on the surface of the redox layer.

The inventor has also found that an ISFET sensor having higher durability and stability and exhibiting outstanding sensor characteristics can be obtained if the sensor includes (a) an electrically conductive layer provided on the surface of a gate isolating layer, (b) an ion-sensitive layer which is not deposited directly on the electrically conductive layer, and (c) a layer having a redox function deposited on the electrically conductive layer so as to intervene between it and the redox layer. The invention has been perfected on the basis of this discovery.

More specifically, the present invention provides an ion-sensitive layer FET sensor characterized by comprising a MOSFET, an electrically conductive layer deposited on the surface of the gate isolating layer, a layer (hereinafter referred to as a redox layer) having a redox function deposited on the surface of the electrically conductive layer, and an ion-sensitive layer deposited on the surface of the redox layer.

Further, the inventor has found that an ISFET electrode exhibiting outstanding sensor characteristics can be obtained if the electrode includes an organic polymeric membrane as a hydrogen ion-sensitive layer, the membrane containing a hydrogen ion carrier substance, described below.

More specifically, the present invention provides an ion-sensitive FET sensor in which a hydrogen ion-sensitive layer is deposited on a MOSFET gate isolation membrane, the hydrogen ion-sensitive layer comprising an organic polymeric membrane containing a hydrogen ion carrier substance, which is a compound expressed by the formula

where $R^1$, $R^2$, $R^3$ represent the same or different alkyl groups, among which at least two alkyl groups have a carbon number of 8-18.

Further, the present invention provides an ion-sensitive FET sensor in which a hydrogen ion-sensitive layer is deposited on a MOSFET gate isolation membrane, the hydrogen ion-sensitive layer comprising an organic polymeric membrane containing a hydrogen ion carrier substance, which is a compound expressed by the formula

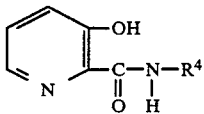

where $R^4$ represents an alkyl group having a carbon number of 8-18, preferably an alkyl group having a carbon number of 10-16.

The MOSFET employed in the present invention is of the type used in ISFETs well-known in the art. If the gate isolation layer (hereinafter also referred to as a gate isolation membrane where appropriate) thereof can be utilized, any MOSFET may be adopted [Matsuo and Esashi, Electrochemistry and Industrial Physics, 50, 64 (1982)]. An example which can be mentioned is one in which a FET having an Si-SiO$_2$ gate isolating layer is formed on a silicon or sapphire substrate. An isolated gate-type MOSFET is also well-suited for use. The MOSFET using the silicon substrate is comparatively low in cost and suited for general-purpose use. The MOSFET employing the sapphire substrate coupled with high density, is readily insulated, lends itself well to miniaturization and excels functionally.

The MOSFET can be fabricated by utilizing conventional planar or ion injection techniques. The gate isolating property can be greatly enhanced by forming an insulating film comprising Si$_3$N$_4$ or the like on the surface of the gate isolating layer of the MOSFET by using a CVD (chemical vapor deposition) technique or a sputtering technique.

To form the electrically conductive layer on the gate isolating layer of the MOSFET, an electrically conductive material is deposited on the surface of the gate isolating layer by evaporation, sputtering, ion plating, CVD, ion beam sputtering, etc. The membrane thickness of the conductive layer is 100 Å to 1 μm, preferably a thickness which is substantially impermeable to light, namely 500 Å to 0.5 μm. Though electrically conductive carbon is best as the electrically conductive material, a material such as carbon, metals and electrically conductive metal oxides may be used without particular limitation so long as it exhibits good adhesion with respect to the gate isolating layer and redox layer. In addition, the electrically conductive layer is not limited to a single layer but can have a multilayer structure. If the multilayer structure is adopted, excellent results are obtained by coating the gate isolating layer with a thin membrane of a metal such as Ni or Cr, and providing another electrically conductive layer on this thin metallic membrane.

The redox layer refers to one in which an electrode comprising an electrically conductive substrate having this layer deposited on its surface is capable of generating a constant potential on the substrate owing to a redox reaction. In the present invention, an especially preferred redox layer is one which will not allow the potential to fluctuate due to the partial pressure of oxygen gas. In a case where the electrically conductive layer is not provided, it is preferred that the redox layer exhibit a reversible oxidation-reduction function. Particularly suitable examples of the redox layer are (1) an organic compound membrane or a polymeric membrane capable of a quinone-hydroquinone type redox reaction, and (2) an organic compound membrane or polymeric membrane capable of an amine-quinoid type redox reaction. The quinone-hydroquinone type redox reaction is expressed by e.g. the following reaction formula, taking a polymer as an example:

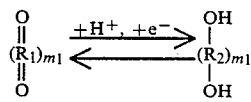

where $R_1$, $R_2$ represent e.g. compounds having a structure containing an aromatic series.

The amine-quinoid type redox reaction is expressed by e.g. the following reaction formula, taking a polymer as an example:

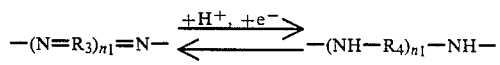

where $R_3$, $R_4$ represent e.g. compounds having a structure containing an aromatic series.

The following compounds (a)-(d) can be mentioned as compounds capable of forming the abovementioned layer having the redox function:

(a) A hydroxy aromatic compound expressed by

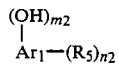

where $Ar_1$ represents an aromatic nucleus, $R_5$ a substituent group, $m_2$ is 1 or the effective valence of $Ar_1$, and $n_2$ is 0 or the effective valence of $Ar_1$ minus 1.

The aromatic nucleus of $Ar_1$ may be a single ring such as a benzene nucleus, a multiple ring such as an anthracene nucleus, pyrene nucleus, chysene nucleus, perylene nucleus or coronene nucleus, or a heterocyclic ring. Examples of the substitutent group $R_5$ are alkyl groups such as a methyl group, aryl groups such as a phenyl group, and a halogen atom. More specifically, examples are dimethyl phenol, phenol, hydroxy pyridine, o- and m-benzyl alcohols, o-, m- and p-hydroxybenzaldehydes, o- and m-hydroxyacetophenones, o-, m- and p-hydroxypro- piophenons, o-, m- and p-hydroxybenzophenones, o-, m- and p-carboxyphenols, diphenylphenol, 2-methyl-8-hydroxyquinoline, 5-hydroxy-1,4-naphthoquinone, 4-(p-hydroxyphenyl)-2-butanone, 1,5-dihydroxy-1,2,3,4-tetrahydronaphthalene, bisphenol-A, salicylanilide, 5- and 8-hydroquinolines, 1,8-dihydroxyanthraquinone, and 5-hydroxy-1,4-naphthoquinone.

(b) An amino aromatic compound expressed by the formula

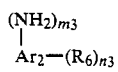

where $Ar_2$ represents an aromatic nucleus, $R_6$ a substituent group, $m_3$ is 1 or the effective valence of $Ar_2$, and $n_3$ is 0 or the effective valence of $Ar_2$ minus 1.

As for the aromatic nucleus $Ar_2$ and the substitution group $R_6$, items similar to $Ar_1$ and the substitution group $R_5$ in compound (a) can be used. Specific examples of the amino aromatic compound are aniline, 1,2-diaminobenzene, aminopyrene, diaminopyrene, aminochrysene, diaminochrysene, 1-aminonaphthalene, 9-aminonaphthalene, 9,10-diaminonaphthalene, 1-aminoanthraquinone, p-phenoxyaniline, o-phenylenediamine, p-chloroaniline, 3,5-dichloroaniline, 2,4,6-trichloroaniline, N-methylaniline, and N-phenyl-p-phenylenediamine.

(c) A quinone such as 1,6-pyrenequinone, 1,2,5,8-tetrahydroxynalizaline, phenantolinequinone, 1-aminoanthraquinone, purpurine, 1-amino-4-hydroxyanthraquinone, and anthralphyne.

Among these compounds, 2,6-xylenol and 1-aminopyrene are especially preferred.

(d) Pyrrole and derivatives thereof (e.g. N-methylpyrrole), and thiophene and derivatives thereof (e.g. methyl thiophene).

Further, examples of compounds capable of forming the layer having the redox function are those which undergo a redox reaction. The following can be mentioned: poly(N-methyl aniline) [Onuki, Matsuda, Koyama, Nihon Kagakkaishi, 1801-1809 (1984)], poly(2k6-dimethyl-1,4-phene ether), poly(o-phenylediamine), poly(phenol) and polyxylenol; organic compounds containing the compounds (a) through (d) such as pyrazoronequinone group-containing vinyl compound-polymers, isoaroxythazine group-containing vinyl compound-polymers and other quinone group-containing compound-polymers, lower polymeric compounds (oligomers) of compounds (a) through (d), or substances obtained by fixing the compounds (a) through (d) to polymeric compounds such as polyvinyl compounds and polyamide compounds. In the present specification, the term "polymer" is taken to mean both homopolymers and mutual polymers such as copolymers.

In the present invention, in order to deposit the compound capable of forming the redox layer on the gate isolating membrane, a polymer obtained by synthesizing an amino aromatic compound, a hydroxy aromatic compound or the like on an electrically conductive substrate of electrically conductive carbon or a precious metal by an electrolytic oxidation polymerization method or electrodeposition method, or a polymer synthesized by application of electron beam irradiation, light or heat, is dissolved in a solvent. The resulting solution is (a) deposited on the gate isolating membrane by painting or dipping, (b) reacted in the gas phase in vacuo and deposited directly on the FET gate isolating membrane, or (c) irradiated with light, heat or radiation to be deposited directly on the FET gate isolating membrane. Among these three methods, the most preferred is that in which the pre-synthesized polymer dissolved in the solvent is deposited by painting or dipping. The electrolytic oxidation polymerization method is implemented by subjecting the amino aromatic compound or hydroxy aromatic compound to electrolytic oxidation polymerization in a solvent in the presence of a suitable supporting electrolyte and depositing a layer of the polymer on the surface of the electrically conductive substrate. Preferred examples of the solvent are acetonitrile, water, dimethyl formamide, dimethyl sulfoxide, propylene carbonate and the like. Preferred examples of the supporting electrolyte are sodium perchlorate, sulfuric acid, sodium sulfate, phosphoric acid, boracic acid, tetrafluoro-potassium phosphate, quaternary ammonium salts and the like.

The membrane thickness of the redox layer is 0.01 $\mu$m-0.5 mm, preferably 0.1-10 $\mu$m. A membrane thickness of less than 0.01 $\mu$m does not fully bring forth the effects of the invention, while a thickness of more than 0.5 mm is undesirable from the viewpoint of miniaturizing the sensor.

The redox layer can be deposited directly on the gate isolating membrane. However, in order to prevent intrusion or leakage of the solution on the gate isolating membrane, it is preferred that the redox layer be deposited after e.g. $SiO_2$ and the $SiO_2$ gate isolating membrane is covered with a membrane of $Si_3N_4$, $Ta_2O_5$ or $Al_2O_3$. As a result of coating the isolated gate with the redox layer in an isolated gate-type ISFET, the FET portion is not exposed to the liquid specimen or to light. This is desirable in that drift generally is reduced.

The redox layer used in the present invention can be used in a form impregnated with an electrolyte. Examples of the electrolyte are phosphoric acid, dipotassium hydrogen phosphate, sodium perchlorate, sulfuric acid, tetrafluoro borate, tetraphenyl borate and the like. In order to impregnate the redox layer with the electrolyte, a simple method which can be adopted is to coat the gate isolating membrane with the redox layer and then dip the resulting membrane into a solution of the electrolyte.

In the present invention, in order to deposit the compound capable of forming the redox layer on the surface of the electrically conductive layer, a polymer obtained by synthesizing an amino aromatic compound, a hydroxy aromatic compound or the like on an electrically conductive substrate of electrically conductive carbon or a precious metal by an electrolytic oxidation polymerization method or electrodeposition method, or a polymer synthesized by application of electron beam irradiation, light or heat, is dissolved in a solvent. The resulting solution is (a) deposited on the surface of the electrically conductive layer by painting or dipping, (b) reacted in the gas phase in vacuo and deposited directly on the FET gate isolating membrane, or (c) deposited directly on the surface of the electrically conductive layer by the electrolytic oxidation polymerization method or by being irradiated with light, heat or radiation. The preferred method among these is direct deposition by electrolytic oxidation polymerization.

The electrolytic oxidation polymerization method is implemented by subjecting the amino aromatic compound or hydroxy aromatic compound to electrolytic oxidation polymerization in a solvent in the presence of a suitable supporting electrolyte and depositing a membrane of the polymer on the surface of the electrically conductive layer. Preferred examples of the solvent are acetonitrile, water, dimethyl formamide, dimethyl sulfoxide, propylene carbonate and the like. Preferred examples of the supporting electrolyte are sodium perchlorate, sulfuric acid, sodium sulfate, phosphoric acid, boracic acid, tetrofluoro-potassium phosphate, quaternary ammonium salts and the like.

The membrane thickness of the redox layer is 0.01 $\mu$m-0.5 mm, preferably 0.1-10 $\mu$m. A membrane thickness of less than 0.01 $\mu$m does not fully bring forth the effects of the invention, while a thickness of more than 0.5 mm is undesirable from the viewpoint of miniaturizing the sensor.

The redox layer used in the present invention can be used in a form impregnated with an electrolyte. Examples of the electrolyte are phosphoric acid, dipotassium hydrogen phosphate, sodium perchlorate, sulfuric acid, tetrafluoro borate, tetraphenyl borate and the like. In order to impregnate the redox layer with the electrolyte, a simple method which can be adopted is to deposit the redox layer on the surface of the electrically conductive layer and then dip the result into a solution of the electrolyte.

Thus, the surface of the redox layer coating the gate isolating membrane or the electrically conductive layer is itself coated with an ion-sensitive layer. As the ion-sensitive layer, use can be made of a membrane (a neutral carrier membrane) in which an ion carrier material selective to the ion of interest and, if necessary, an electrolytic salt, are carried on a polymeric compound. The following are examples of the ion carrier material which can be used, depending upon the ion of interest:

(i) For hydrogen ion

Examples of a hydrogen ion carrier material, are amines expressed by the formula

(where $R^7$, $R^8$, $R^9$ represent the same or different alkyl groups, among which at least two alkyl groups have a carbon number of 8–18), and compounds expressed by the formula

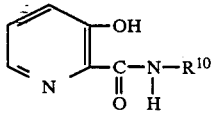

(where $R^{10}$ represents an alkyl group having a carbon number of 8–18). Tri-n-dodecylamine is especially preferred. Most preferred is tridodecylamine.

(ii) For potassium ion

Examples of which can be mentioned are valinomycin, nonactin, monoactin, crown ether compounds such as dicyclohexyl-18-crown-6, naphtho-15-crown-5, bis(15-crown-5) and the like. Among these, valinomycin and bis(15-crown-5) are ideal.

(iii) For sodium ion

Examples which can be mentioned are aromatic amides or diamides, aliphatic amides or diamides, and crown compounds, e.g. bis[12-crown-4)methyl] dodecylmalonate, N,N,N,N-tetrapropyl-3,6-dioxanate diamide, N,N,N,N-tetrabenzyl-1,2-ethenedioxy diacetoamide, N,N′-dibenzyl-N,N′-diphenyl-1,2-phenyldiacetamide, N,N′,N″-triheptyl-N,N′N″-trimethyl-4,4′,4″-propylpyridine tris(3-oxythabutylamide), 3-methoxy-N,N,N,N-tetrapropyl-1,2-phenyldioxydiacetopropyl-1,2-phenylene dioxydiacetoamide, (−)-(R,R)-4,5-dimethyl-N,N,N,N-tetrapropyl-3,6-dioxaoctanediamide, 4-methyl-N,N,N,N-tetrapropyl-3-6-dioxaoctane diamide, N,N,N,N-tetrapropyl-1,2-phenylenedioxydiacetoamide, N,N,N,N-tetrapropyl-2,3-naphthandedioxydiacetoamide, 4-t-butyl-N,N,N,N-tetrapropyl-1,2-dichlorohexanedioxydiacetoamide, cis-N,N,N,N-tetrapropyl-1,2-cyclohexanedioxydiacetoamide, and trans-N,N,N,N-tetrapropyl-1,2-cyclohexanedioxydiacetoamide. Among these, bis[(12-crown-4)methyl] dodecylmalonate is well-suited for use.

(iv) For chlorine ion

Examples which can be mentioned are quaternary ammonium salts expressed by the formula

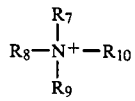

(where $R^7$, $R^8$, $R^9$ represent the same or different alkyl groups having a carbon number of 8–18, and $R_{10}$ represents hydrogen or an alkyl group having a carbon number of 1–8, and a triphenyl tin chloride expressed by the formula

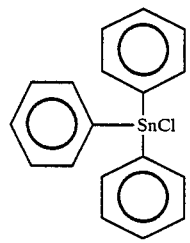

(v) For calcium ion

Suitable examples are bis[di-(octyphenyl)phosphate], (−)-(R,R)-N,N′-bis[11-ethoxy carbonyl)undecyl]-N,N′,4,5-tetramethyl-3,6-dioxaoctane-diamide and calcium bis[di(n-decyl)phosphate].

(vi) For hydrogencarbonate ion

Examples which can be mentioned are a quaternary ammonium salts expressed by the formula

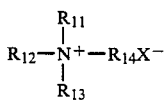

(where $R_{11}$, $R_{12}$, $R_{13}$ represent the same or different alkyl groups having a carbon number of 8–18, $R_{14}$ represents hydrogen atom or an alkyl group having a carbon number of 1–4, and $X^-$ represents $Cl^-$, $Br^-$ or $OH^-$), tertiary amine compounds expressed by the formula

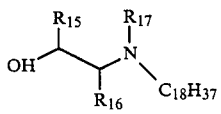

(where $R_{15}$ represents a phenyl group, hydrogen atom or a methyl group, $R_{16}$ represents hydrogen atom or a methyl group, and $R_{17}$ represents a methyl group or an octadecyl group), and a compound expressed by the formula

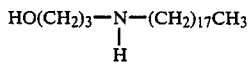

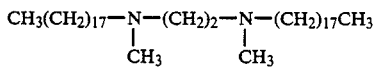

Examples of the electrolytic salt are sodium tetrakis(p-chlorophenyl)borate, potassium tetrakis(p-chlorophenyl)borate, and a compound expressed by the formula

where $R_{18}$ represents an alkyl group, preferably an alkyl group having a carbon number of 2–6.

Examples of the polymer compound are organic polymer compounds such as vinyl chloride resin, vinyl chloride-ethylene copolymer, polyester, polyacryl amide and polyurethane, and inorganic polymer compounds such as silicone resin. Compounds are used in which the plasticizer does not readily elute. Examples of such a plasticizer are dioctyl sebacate ester, dioctyl adipate ester, dioctyl maleate ester and di-n-octyl phenylphosphonate.

In order to coat the surface of the redox layer on the MOSFET gate isolating membrane with the ion-sensitive layer having the foregoing composition, 50–100 parts by weight of the plasticizer, 0.1–50 parts by weight of the ion carrier material (both with respect to 100 parts by weight of the polymer compound serving as the carrier) and the electrolytic salt are dissolved in a solvent (e.g. tetrahydrofuran). The resulting solution is placed on the gate isolating membrane to a thickness of 0.1 μm–10 mm and is then dried at room temperature or under heating. Alternatively, the gate isolating membrane is dipped into the solution followed by drying in a similar manner. It is desired that the thickness of the applied ion-sensitive layer be 10 μm–1 mm.

Since the gate isolating membrane of the MOSFET is coated with the ion-sensitive layer through the intermediary of the redox layer, the ISFET sensor of the present invention exhibits excellent membrane adhesion and water resistance. Furthermore, since the MOSFET has a high input impedance, the ISFET sensor of the invention operates stably even if the applied ion-sensitive layer has a high resistivity. Since the amplifying action thereof can be utilized, the sensor has a quick response and excellent ion selectivity despite is small size. Measurements can be taken inside a living body by using the sensor in a catheter or the like. Moreover, the sensor exhibits good potential stability and little drift, and the influence of blood components can be reduced.

In another aspect of the invention, the ISFET sensor has the electrically conductive layer provided on the surface of the MOSFET gate isolating layer, and the ion-sensitive layer is deposited on the electrically conductive layer through the intermediary of the redox layer. Accordingly, the membranes exhibit good adhesion and durability. In addition since the sensor is not readily influenced by light, potential drift is very slight and stability is outstanding. Since the MOSFET has a high input impedance, the ISFET sensor of the invention operates stably even if the applied ion-sensitive layer has a high resistivity. Since the amplifying action thereof can be utilized, the sensor has a quick response despite its small size.

Further, the ISFET electrode of the invention uses an organic polymeric membrane as a hydrogen ion-sensitive layer, the membrane containing a neutral carrier material which includes an amine-type hydrogen ion carrier substance. The ISFET electrode of the invention, which has sensor characteristics equivalent to those of the conventional article using a chemically stable membrane of $Al_2O_3$ or $Ta_2O_5$, makes possible rapid and stable measurement of pH.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 2 is a schematic sectional view taken along line A—A' of the ISFET sensor shown in FIG. 1 and fabricated according to an example of the invention;

FIG. 3 is a schematic sectional view taken along line B—B' of the ISFET sensor shown in FIG. 1 and fabricated according to an example of the invention;

FIG. 12 is a schematic sectional view of the ISFET sensor fabricated according to the seventh example of the invention;

FIG. 13 is a schematic sectional view showing a gate portion of a pH measuring-type ISFET sensor fabricated according to an eighth example of the invention;

FIG. 14 is a schematic sectional view showing a gate portion of a pH measuring-type ISFET sensor fabricated according to a ninth example of the invention;

FIG. 18 is a view in which source voltage is plotted against pH when a pH measurement is made using a MOSFET having a neutral carrier membrane deposited thereon;

DESCRIPTION OF THE PREFERRED EMBODIMENT

The present invention will now be described with regard to a number of examples and experiments.

EXAMPLE 1

An ISFET sensor was fabricated by coating the surface of a redox layer on the gate isolating membrane of a MOSFET with a potassium ion-sensitive layer. The method of fabrication will now be described, with FIG. 1 being a schematic view of the ISFET sensor, FIG. 2 a schematic sectional view taken along line A—A' of FIG. 1, and FIG. 3 a schematic sectional view taken along line B—B' of FIG. 1.

(1) MOSFET

Figure 1:
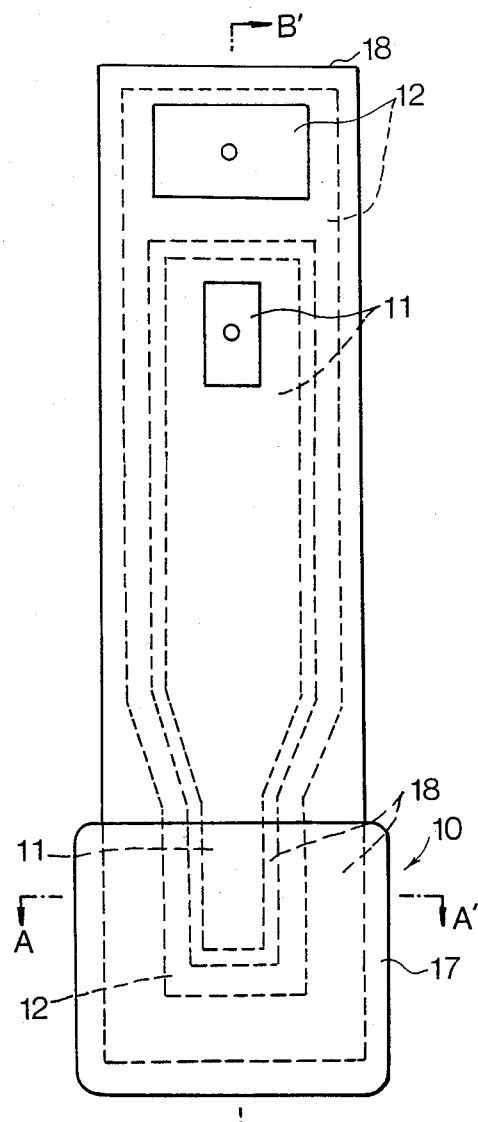
FIG. 1 is a schematic view of an ISFET sensor.

To fabricate the MOSFET, use was made of a FET (a so-called isolated-type FET) of needle-like structure whose gate portion was extended into the tip. The FET was formed by laminating a p-type silicon wafer with a p-type Si—SiO$_2$ gate isolating membrane. A MOSFET of this type can be fabricated by utilizing an ordinary planar technique. In FIG. 1, numeral 10 denotes the gate portion, 11 a drain and 12 a source. In FIGS. 2 and 3, numeral 13 designates the SiO$_2$ membrane, 14 an insulating membrane such as Si$_3$N$_4$, and 18 a silicon substrate.

(2) Redox layer (numeral 16)

Electrolyte
0.5M 2,6-xylenol
0.2M NaClO$_4$
acetonitrile (solvent)
Electrolytic conditions
−20° C.

After the electrolytic potential was swept three times from 0 V to 1.5 V vs. SSCE (saturated sodium chloride saturated calomel electrode) (scan rate: 50 mV/sec), constant potential electrolysis was performed at 1.5 V for 10 min.

An oxidation polymeric membrane was obtained by performing electrolysis under the above conditions using a BPG electrode having a surface area of 5 cm$^2$. After being washed in the cold acetonitrile solvent, the membrane was dissolved in 1 ml of methanol. The gate portion of the MOSFET was dipped into the dipping solution thus prepared or was painted with the dipping solution, followed by drying. A redox layer having a thickness of 2-3 μm was thus formed.

(3) Potassium ion-sensitive layer (numeral 17)

A potassium ion carrier composition (described below) containing valinomycin was placed on the surface of the redox layer coating the SiO$_2$ membrane of the MOSFET gate portion. This was followed by blow-drying to form a coating of a potassium ion-sensitive layer having a thickness of about 0.4 mm.

| Potassium ion carrier composition | |
|---|---|
| valinomycin | 3.2 mg/ml |
| polyvinyl chloride (p$_n$ = 1050) | 65.6 mg/ml |
| di(2-ethyl hexyl) sebacate | 131.2 mg/ml |

| Potassium ion carrier composition | |
|---|---|
| solvent: tetrahydrofuran (THF) | |

EXPERIMENT 1a

Figure 4:
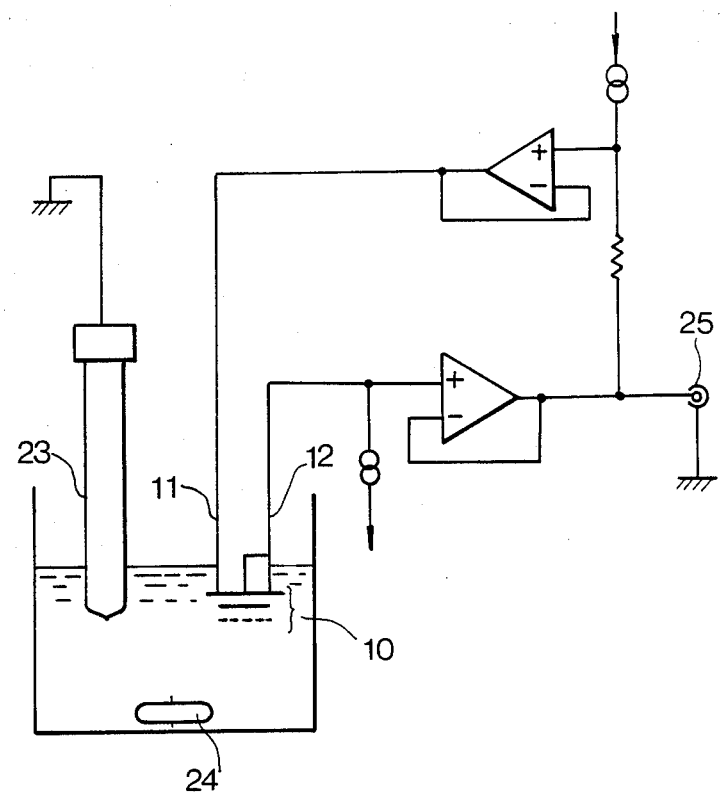
FIG. 4 is a schematic explanatory view illustrating a cell for measuring ionic concentration by means of the ISFET sensor of the invention, as well as a circuit for measuring source voltage (Vout) with respect to a reference electrode.

Using the potassium ion ISFET sensor fabricated in Example 1 as the active electrode and an SSCE as a reference electrode, a measurement cell and a measurement circuit were set up as shown in FIG. 4 and source voltage (Vout) with respect to the reference electrode was measured in a standard solution. In FIG. 4, numeral 23 denotes the reference electrode, 24 a stirrer and 25 the source voltage (Vout). The condition of measurement is that source-drain voltage (V$_{DS}$) is 4 V, and that the temperature of a measured solution is 37° C. Vout of the ISFET was measured usiang a digital multimeter (TR6841, manufactured by Advantest Corporation). A $10^{-4}-5\times10^{-1}$M KCl solution was used as the standard solution. Measurement was made at a temperature of 36.4° C. in the atmosphere and under constant illumination while the liquid specimen was stirred. When the measured source voltage Vout is plotted against the potassium ion concentration, the result is the graph shown in FIG. 5.

Figure 5:
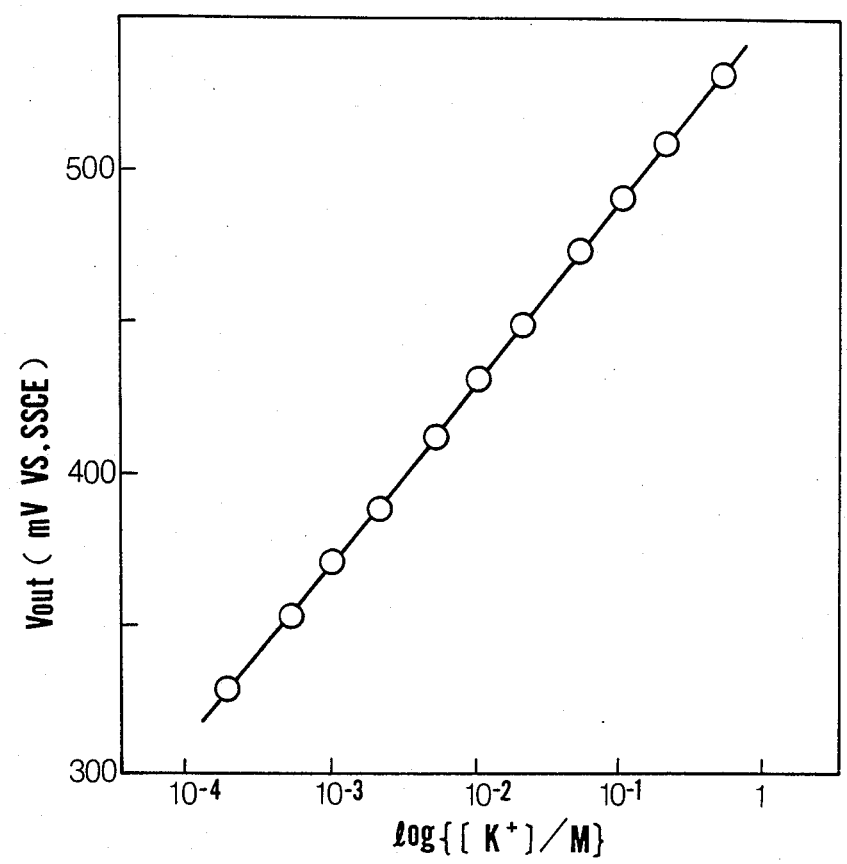
FIGS. 5 through 9 are views in which Vout of sensors fabricated in accordance with first through fifth examples of the present invention, respectively, are plotted against ionic concentrations, in which FIG. 5 relates to potassium ion, FIG. 6 sodium ion, FIG. 7 chlorine ion, FIG. 8 calcium ion and FIG. 9 hydrogencarbonate ion.

The graph of FIG. 5 shows that the plot of Vout against potassium ion concentration has excellent linearity over the range of $10^{-4}-5\times10^{-1}$M. The slope of the straight line is 59.8 mV/log [(K$^+$)/M]. The speed of response was confirmed to be very high, namely within one second at a response of 95% when the sensor, at equilibrium in a 1 mM KCL solution, was dipped into a 100 mM KCl solution.

EXPERIMENT 1b

Sodium ion, ammonium ion and hydrogen ion were each added at a concentration of 100 mM to the standard solution of Experiment 1a and measurement was performed as in Experiment 1a, whereby the selection coefficients of the potassium ion ISFET sensor of the invention were obtained with respect to the various cations. The results obtained were, respectively, log $K_{K^+ \cdot Na^+}{}^{Pot} = -4.0$, log $K_{K^+ \cdot NH_4^+}{}^{Pot} = -2.0$, log $K_{K^+ \cdot H^+}{}^{Pot} = -4.3$.

These results demonstrate that the potassium ion ISFET sensor of the invention is capable of measuring potassium ion, without interference from coexisting cations, even if the liquid specimen is blood serum, blood or the like.

EXAMPLE 2

A sodium ion ISFET sensor was fabricated as in Example 1 except for the fact that a sodium ion carrier composition (described below) was used as the ion carrier composition. The sodium ion-sensitive layer coating had a thickness of about 0.5 mm.

| Sodium ion carrier composition | |
|---|---|
| bis[(12-crown-4) methyl] dodecyl malonate (Dojindo Laboratories) | 5.98 mg/ml |
| potassium tetrakis(p-chlorophenyl) borate (Dojindo Laboratories) | 1.01 mg/ml |
| polyvinyl chloride (p$_n$ = 1050) | 64.94 mg/ml |
| di(2-ethyl hexyl) sebacate | 129.0 mg/ml |
| solvent: THF | |

After being dried sufficiently, the sodium ion ISFET sensor fabricated as set forth above was dipped in a 1 mM NaCl aqueous solution for two hours and then subjected to an experiment.

EXPERIMENT 2

Vout was measured as in Experiment 1a except for the fact that the sodium ion ISFET sensor obtained in Example 2 was used as the ISFET and a $0.5 \times 10^{-3} - 5 \times 10^{-1}$M NaCl solution was employed as the standard solution. The measurement conditions such as temperature were the same as in Experiment 1a. The results are shown in FIG. 6.

Figure 6:
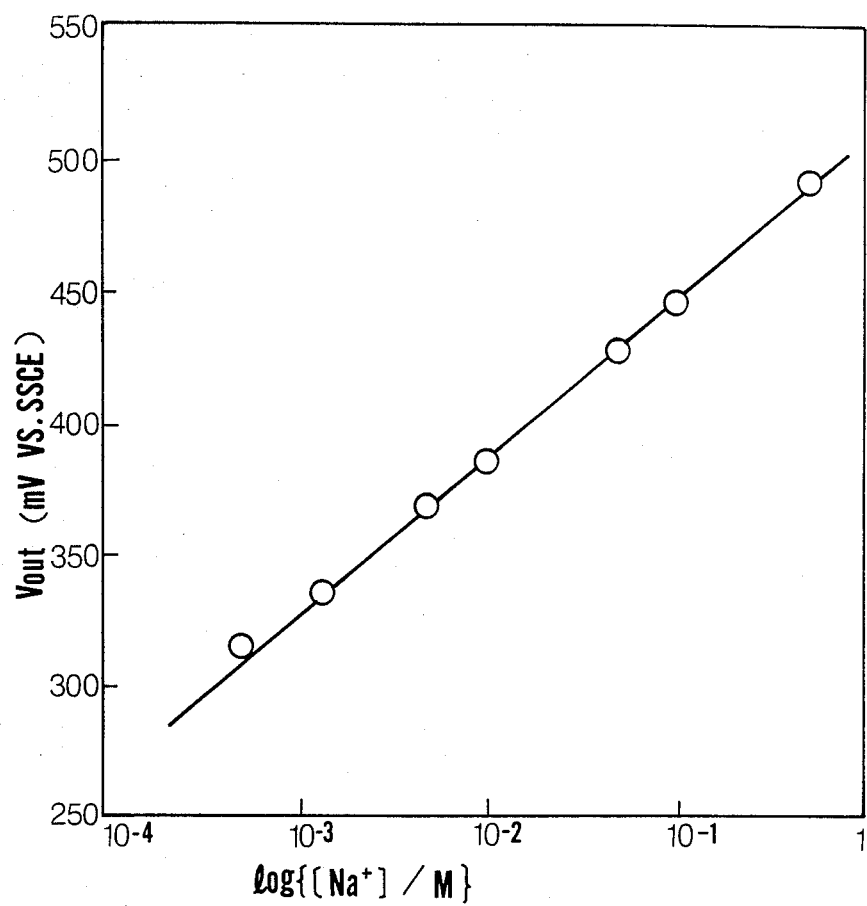

The graph of FIG. 6 shows that the plot of Vout against sodium ion concentration has excellent linearity over the range of $10^{-3} - 5 \times 10^{-1}$M. The slope of the straight line is 59.7 mV/log [(Na+)/M]. The speed of response was within one second at a response of 95%. The selection coefficients with respect to the other cations, measured as in Example 1b, were log $K_{Na+\cdot K+}{}^{Pot} = -2.0$ and log $K_{Na+\cdot NH4+}{}^{Pot} = -2.7$.

EXAMPLE 3

A chlorine ion ISFET sensor was fabricated as in Example 1 except for the fact that a chlorine ion carrier composition (described below) was used as the ion carrier composition. The chlorine ion-sensitive layer coating had a thickness of about 0.5 mm.

| Chlorine ion carrier composition | |
|---|---|
| triphenyl tin chloride | 15.2 mg/ml |
| polyvinyl chloride ($p_n$ = 1050) | 63.0 mg/ml |
| di(2-ethyl hexyl) sebacate | 125.8 mg/ml |
| solvent: THF | |

After being dried sufficiently, the chlorine ion ISFET sensor fabricated as set forth above was dipped in a 1mM NaCl aqueous solution for two hours and then subjected to an experiment.

EXPERIMENT 3

Vout was measured as in Experiment 1a except for the fact that the chlorine ion ISFET sensor obtained in Example 3 was used as the ISFET and a $2 \times 10^{-4} - 5 \times 10^{-1}$M NaCl solution was employed as the standard solution. The measurement temperature was 37° C., with the other measurement conditions being the same as in Experiment 1. The results are shown in FIG. 7.

Figure 7:
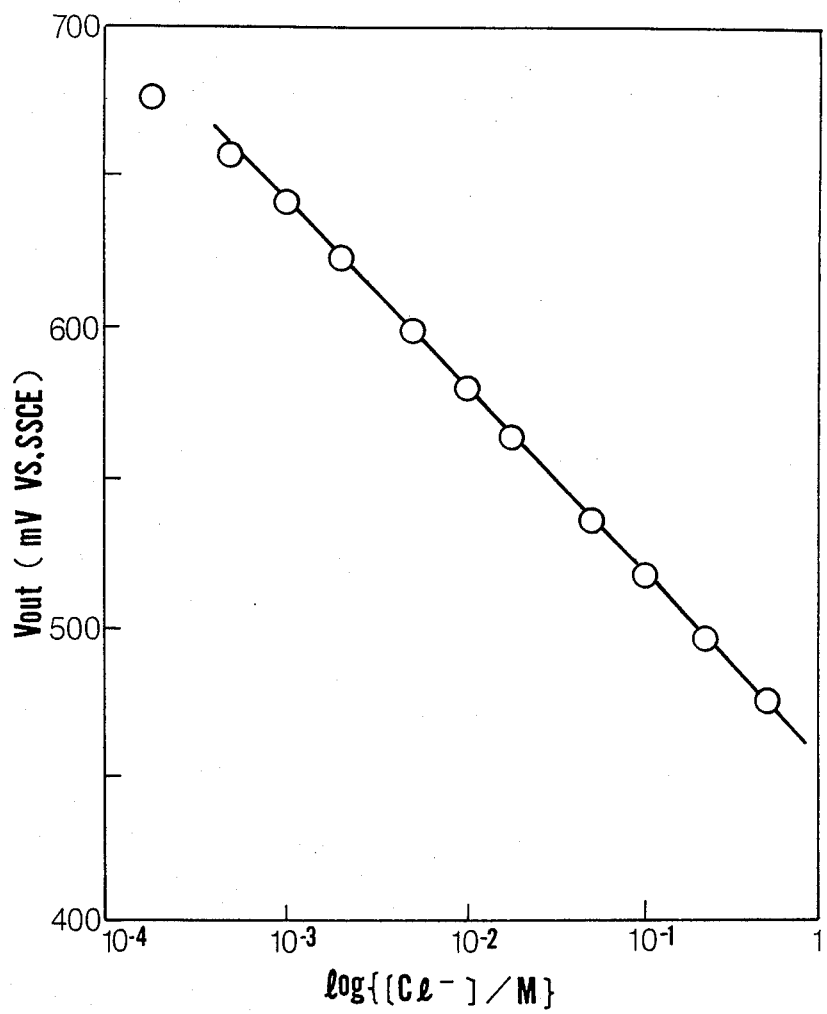

The graph of FIG. 7 shows that the plot of Vout against chlorine ion concentration has excellent linearity over the range of $10^{-3} - 5 \times 10^{-1}$M. The slope of the straight line is $-61.2$ mV/log [(Cl−)/M]. The speed of response was within one second at a response of 95% for a concentration of $10^{-2} - 5 \times 10^{-1}$. The selectivity coefficient with respect to perchloric acid ion, measured as in Example 2, was log $K_{Cl-\cdot ClO4}{}^{Pot} = -2.5$. It was thus clarified that the sensor is little affected by coexisting cations.

EXAMPLE 4

A calcium ion ISFET sensor was fabricated as in Example 1 except for the fact that a calcium ion carrier composition (described below) was used as the ion carrier composition. The calcium ion-sensitive layer coating had a thickness of about 0.4 mm.

| Calcium ion carrier composition | |
|---|---|
| calcium bis[di-(n-octyl phenyl) phosphate] | 14.0 mg/ml |
| di-(n-octyl phenyl) phosphate | 62.0 mg/ml |
| polyvinyl chloride | 62.0 mg/ml |
| di(2-ethyl hexyl) sebacate | 62.0 mg/ml |
| solvent: THF | |

EXPERIMENT 4

Vout was measured as in Experiment 1a except for the fact that the calcium ion ISFET sensor obtained in Example 4 was used as the ISFET and a $10^{-4} - 2 \times 10^{-1}$M calcium chloride solution was employed as the standard solution. The measurement temperature was 37° C., with the other measurement conditions being the same as in Experiment 1a. The results are shown in FIG. 8.

Figure 8:
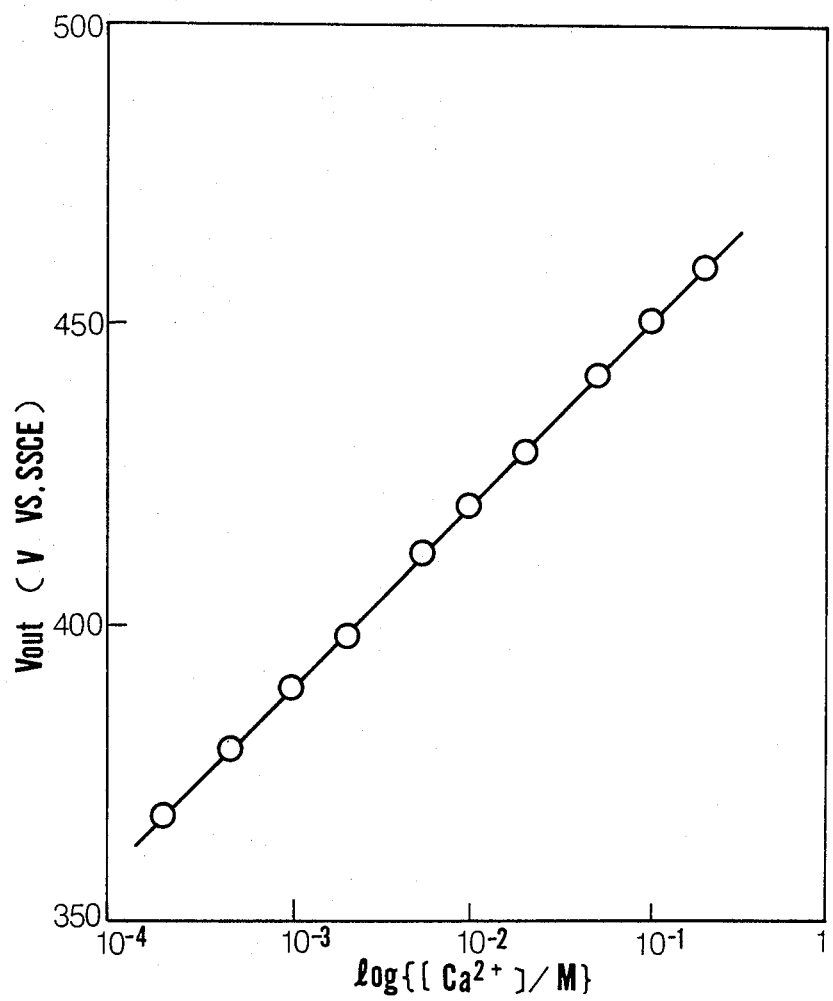

The graph of FIG. 8 shows that the plot of Vout against calcium ion concentration has excellent linearity over the range of $10^{-4} - 2 \times 10^{-1}$M. The slope of the straight line is 30.4 mV/log [(Ca$^{2+}$)/M]. The speed of response of this electrode was within ten seconds at a response of 95%. The selectivity coefficients with respect to the other cations, measured as in Example 1b, were log $K_{Ca2+\cdot Na+}{}^{Pot} = -3.2$ and log $K_{Ca2+\cdot Mg2+}{}^{Pot} = -3.3$. Thus it was clarified that the speed of the response and selectivity were excellent.

EXAMPLE 5

A hydrogencarbonate ion ISFET sensor was fabricated as in Example 1 except for the fact that a hydrogencarbonate ion carrier composition (described below) was used as the ion carrier composition. The hydrogencarbonate ion-sensitive layer coating had a thickness of about 0.5 mm.

| hydrogencarbonate ion carrier composition | |
|---|---|
| tri(n-dodecyl) ammonium chloride | 6.6 mg/ml |
| di(2-ethyl hexyl) sebacate | 128.8 mg/ml |
| polyvinyl chloride ($p_n$ = 1050) | 64.6 mg/ml |
| solvent: THF | |

EXPERIMENT 5

Vout was measured as in Experiment 1a except for the fact that the hydrogencarbonate ion ISFET sensor obtained in Example 5 was used as the ISFET and a $10^{-3} - 10^{-1}$M sodium acid hydrogencarbonate solution was employed as the standard solution. The measurement temperature was 37° C., with the other measurement conditions being the same as in Experiment 1a. The results are shown in FIG. 9.

Figure 9:
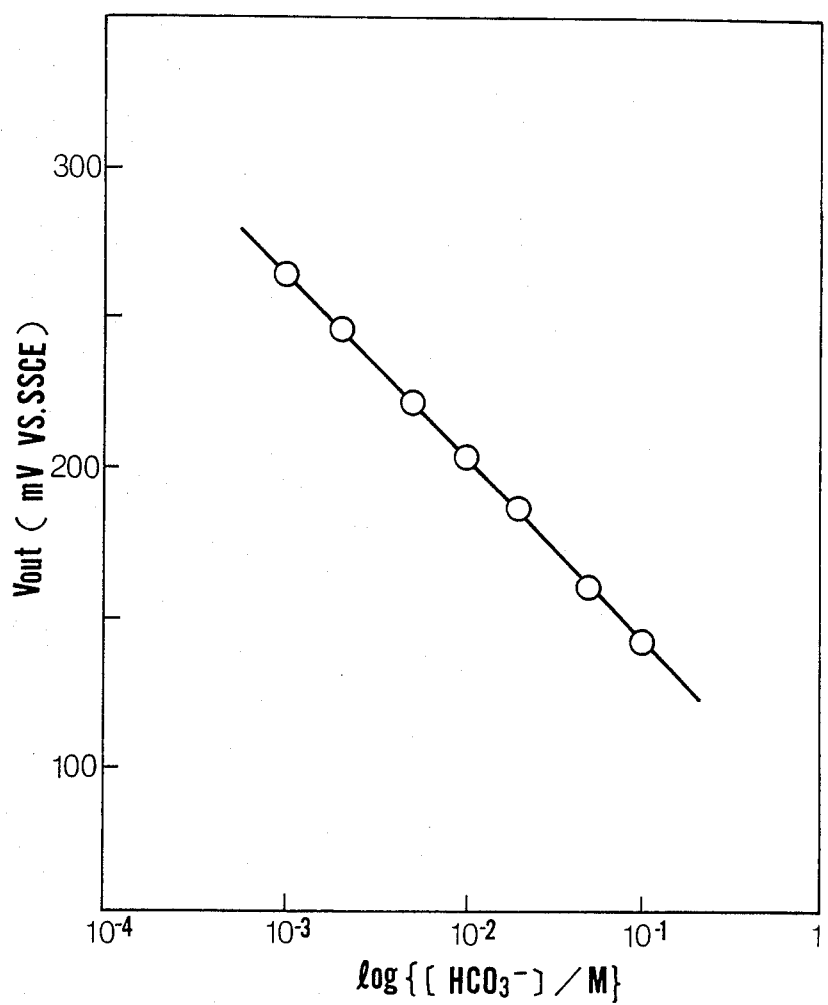

The graph of FIG. 9 shows that the plot of Vout against hydrogencarbonate ion concentration has excellent linearity over the range of $10^{-3} - 10^{-1}$M. The slope of the straight line is 60.7 mV/log [(HCO$_3$−)/M].

EXAMPLE 6

Figure 10:
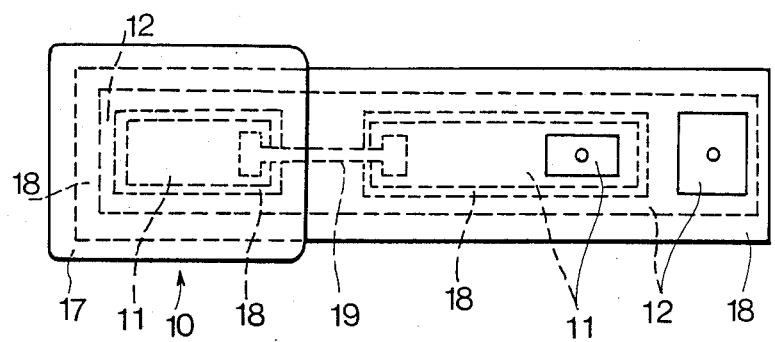
FIG. 10 is a view illustrating an example of an isolated gate-type ISFET sensor.

Instead of the MOSFET employed in Example 1, use was made of a MOSFET having the isolated gate portion 10, as shown in the schematic view of FIG. 10. A polymeric membrane capable of a redox reaction was deposited on the isolated gate portion 10 in the same manner as Example 1, and the surface of the polymeric membrane was coated with a potassium ion-sensitive layer to fabricate an isolated gate-type potassium ion ISFET sensor.

The performance of the sensor thus obtained was the same as that of the sensor in Example 1, but the drift in this case was reduced by an even greater degree.

EXAMPLE 7

Figure 11:
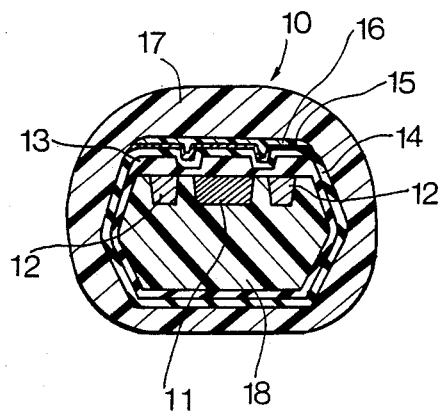
FIG. 11 is a schematic sectional view of an ISFET sensor fabricated according to a seventh example of the invention.

An ISFET sensor for pH measurement was fabricated by forming an electrically conductive carbon membrane on the the surface of the gate isolating layer of a MOSFET, forming a redox membrane on the carbon membrane, and forming a hydrogen ion-sensitive layer on the redox membrane. The method of fabrication will now be described, with FIG. 11 being a schematic sectional view taken along line A—A', and FIG. 12 being a schematic sectional view taken along line B—B'. Numeral 15 denotes the electrically conductive layer.

(1) MOSFET

To fabricate the MOSFET, use was made of a FET (a so-called isolated-type FET) formed by laminating a p-type silicon wafer with a p-type Si-SiO$_2$ gate isolating membrane. A MOSFET of this type is fabricated on the p-type silicon wafer by utilizing an ordinary planar technique which relies upon photolithograpy, and a sputtering method is used to form the coating of the insulating membrane 14 comprising silicon nitride.

(2) Electrically conductive layer 15

Through use of an ion beam sputtering method, an electrically conductive carbon membrane (thickness: 2000 Å) was formed as the electrically conductive layer 15 on the surface of the gate isolating membrane 14 of the MOSFET fabricated in the manner set forth above.

(3) Redox layer 16

Next, electrical contact was made with one end of the carbon membrane 15 by means of a metal contactor and the redox membrane 16 was deposited by carrying out electrolytic oxidation under conditions described below in an electrolyte having the composition given hereunder. In performing electrolysis, a platinum mesh was used as the opposing electrodes, and a saturated sodium chloride saturated calomel electrode (SSCE) was used as the reference electrode.

Electrolyte 0.5M 2,6-dimethyl phenol
0.2M NaClO$_4$
solvent: acetonitrile

Electrolytic conditions

After the electrolytic potential was swept three times from 0 V to 1.5 V vs. SSCE (scan rate: 50 mV/sec), constant potential electrolysis (−20° C.) was performed at 1.5 V for 10 min.

Thus, a plymeric membrane (thickness: about 1 um) capable of a quinone-hydroquinone type redox reaction was formed as the redox membrane.

(4) Hydrogen ion-sensitive layer 17

The electrode coated with the redox layer 16 was itself coated with a hydrogen ion-sensitive membrane (thickness: 0.4 mm) by being painted with a hydrogen ion carrier compositon of the following composition, which was then allowed to dry:

| Hydrogen ion carrier composition | |
|---|---|
| Tridodecyl amine | 2 mg/ml |
| potassium tetrakis(p-chlorophenyl) borate (KT$_p$ClPB, Dojindo Laboratories) | 1.2 mg/ml |
| polyvinyl chloride (PVC, mean degree of polymerization p$_n$ = 1050) | 65.6 mg/ml |
| di(2-ethyl hexyl) sebacate (DOS) | 131.2 mg/ml |
| solvent: THF | |

EXPERIMENT 7

The characteristics of the pH measuring ISFET sensor fabricated in Example 7 were investigated by measuring the sensor source voltage (Vout) with respect to SSCE using the measurement circuit and apparatus shown in FIG. 4. For the measurement of Vout, a digital voltmeter (TR6841, Advantest Corporation) was used. In addition, a 50 mM phosphate buffer solution was used as the liquid specimen. Measurement was made at a temperature of 37° C. over a pH range of 5-9 in the atmosphere and under constant illumination while the liquid specimen was stirred.

The response characteristic with respect to pH exhibited a linear relationship in accordance with a Nernst equation expressed by E=E°—S pH (where E stands for electromotive force, E° for constant potential and S for slope). It was found that S=61 mV/pH (37° C.), and a value close to the theoretical value was obtained. Also, it was clarified that 99% response was within 5 sec, which is a very rapid response, that Vout is constant within an experimental error of ±1 mV, even when the degree of illumination was varied over a range of from 0 to 10,000 lux, and that the sensor is little influenced by light.

Figure 16:
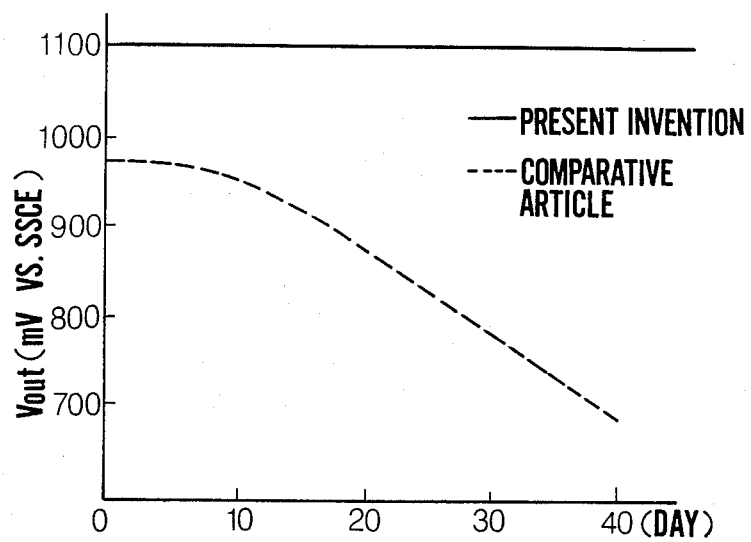
FIG. 16 is a view showing how Vout of the inventive ISFET sensor and Vout of a comparative sensor changes with the passage of time.
Figure 17:
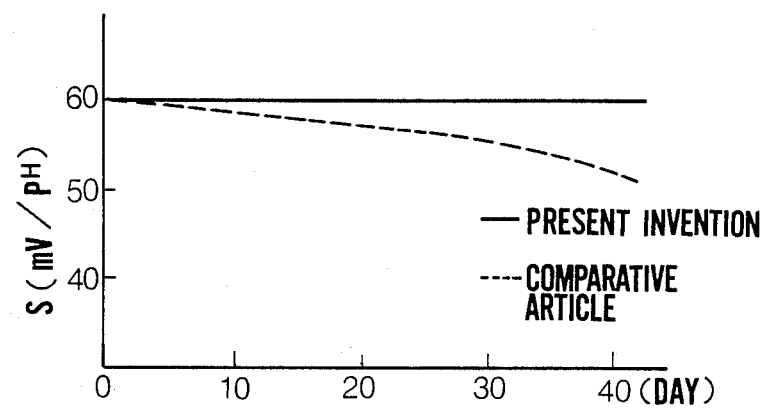
FIG. 17 is a view showing how the slope S of a Nernst plot changes with time for the ISFET of the present invention and for a comparative sensor.

Further, the stability of this pH sensor with the passage of time was investigated by repeating the above-described measurement over a period of 40 days. The results are as shown in FIGS. 16 and 17. The comparative article used was a sensor obtained by depositing a hydrogen ion carrier membrane directly on a gate isolating layer.

As shown in FIGS. 16 and 17, the sensor of the present invention does not exhibit any change in sensor characteristics over a period of more than one month. By contrast, the comparative article shows very little stability.

EXAMPLE 8

A pH measuring ISFET was fabricated as in Example 7 except for the fact that a sapphire substrate was used as the substrate of the MOSFET. A schematic sectional view of the gate portion is illustrated in FIG. 13, in which numeral 20 denotes p-type silicon and numeral 21 denotes an SOS substrate.

EXAMPLE 9

Figure 15:
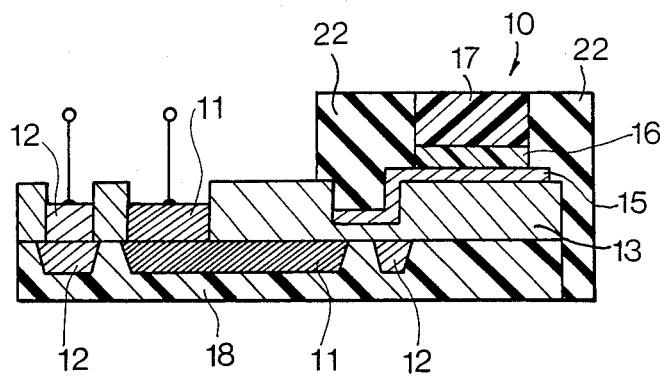
FIG. 15 is a schematic sectional view taken along line C—C of the ISFET sensor shown in FIG. 14.

A pH measuring ISFET was fabricated as in Example 7 except for the fact that a so-called isolated gate-type MOSFET having a structure shown in the schematic views of FIGS. 14 and 15 was used as the substrate of the MOSFET. Numeral 22 designates an insulator.

EXPERIMENTS 8, 9

The ISFETs obtained in Examples 8 and 9 were submitted to measurements similar to those performed in Experiment 7. The results were similar to those obtained in Experiment 7.

EXAMPLE 10

An ISFET sensor for measuring potassium ion concentration was fabricated as in Example 7 except for the fact that a potassium ion carrier composition, described below, was used instead of the hydrogen ion carrier composition in Example 7 and the redox membrane was coated with a potassium ion-sensitive membrane (thickness: 0.4 mm)

| Potassium ion carrier composition | |
|---|---|
| valinomycin | 3.2 mg/ml |
| PVC | 65.6 mg/ml |
| solvent: THF | 131.2 mg/ml |

EXPERIMENT 10

The response characteristics of the ISFET for potassium ion concentration measurement obtained in Example 10 were investigated in the manner set forth in Experiment 7.

The logarithmic value of Vout and potassium ion concentration exhibited good linearity in the range $10^{-4} - 5 \times 10^{-1}$, and the slope of the straight line was 60 mV/log [k+]. It was found that the speed of response was very high, being within one second at a response of 95%, that there was very little change with a change in degree of illumination, and that characteristics were stable for over one month.

EXAMPLES 11-16

Ionic concentration measuring ISFETs shown in Table 1 were fabricated as in Example 7 except for the fact that ion carrier compositions indicated in Table 1 were used instead of the hydrogen ion carrier composition in Example 7 and the redox membrane was coated with an ion-sensitive membrane of thickness 0.3 mm.

TABLE 1

| Example | Ion Specimen | Carrier Material** | Ion Carrier Composition* (content) | KTpClPB | PVC | DOS |
|---|---|---|---|---|---|---|
| 11 | NH4+ | nonactin (contains 25% monactin) | 6.25 mg/ml | 1.25 mg/ml | 80.8 mg/ml | 161.8 mg/ml |
| 12 | Na+ | Bis-12-Crown-4 | 5.0 | 1.1 | 65.0 | 129 |
| 13 | Cl− | TPSnCL | 11.2 | — | 63.0 | 125.8 |
| 14 | HCO3− | TDDA—Cl | 6.6 | — | 64.6 | 128.8 |
| 15 | Ca2+ | Ca(DOPO)2 DOPO | 14.0 62.0 | — | 62.0 | 62.0 |
| 16 | Mg2+ | DHDMBA | 6.25 | 1.25 | 80.5 | 160 |

*All solvents are THF.
**The actual names of the carrier materials, abbreviated in the above table, are given on the following page.

bis-12-crown-4: bis[(12-crown-4)methyl]dodecyl malonate (manufactured by Dojindo Laboratories)
  TPSnCl: triphenyl tin chloride (manufactured by Aldrich)
TDDa-Cl: tridodecyl ammonium chloride
Ca(DOPO)2: calcium bis[di-(n-octyl phenyl)phosphate] (manufactured by Dojindo Laboratories)
DOPO: di(n-octyl phenyl)phosphate (Dojindo Laboratories)
DHDMBA: N,N'-diheptyl-N,N'-dimethyl-1,4-butane diamide (manufactured by FluKa)

EXAMPLE 17

An ISFET sensor was fabricated by coating the surface of a redox layer on the gate isolating membrane of a MOSFET with a hydrogen ion-sensitive layer. The method of fabrication will now be described.

(1) MOSFET

To fabricate the MOSFET, use was made of a FET (a so-called isolated-type FET) of needle-like structure whose gate portion was extended into the tip. The FET was formed by laminating a p-type silicon wafer with a p-type Si-SiO2 gate isolating membrane. A MOSFET of this type can be fabricated by utilizing an ordinary planar technique.

(2) Electrically conductive layer

Through use of an ion beam sputtering method, the surface of the gate isolating membrane of the MOSFET fabricated in the manner set forth above was coated with an electrically conductive carbon membrane to a thickness of 100–5000 Å.

(3) Redox layer

Electrolyte
0.5M pyrrole
0.2M NaClO4
acetonitrile (solvent)
Electrolytic conditions
−20° C.
After the electrolytic potential was swept three times from 0 V to 1.5 V vs. SSCE (scan rate: 50 mV/sec), constant potential electrolysis was performed at 1.5 V for 10 min.

Electrical contact was made with one end of the gate isolating membrane of the carbon-coated MOSFET by means of a metal contactor and electrolytic oxidation was carried out under the above-described conditions to apply a coating of a redox layer to a thickness of 0.1–1.0 μm.

(4) Hydrogen ion-sensitive layer

A hydrogen ion carrier composition, described below, containing tridodecyl amine was painted on the redox layer-coated gate isolating membrane of the MOSFET and allowed to dry. By repeating this process, a hydrogen ion-sensitive layer was formed to a thickness of 200–300 μm.

| Hydrogen ion carrier composition | |
|---|---|
| dodecyl amine | 2.3 mg/ml |
| potassium tetrakis(p-chloro phenyl) borate | 1.0 mg/ml |
| polyvinyl chloride (PVC: $p_n$ = 1050) | 32.4 mg/ml |
| di(2-ethyl hexyl) sebacate (DOS) | 64.8 mg/ml |
| solvent: tetrahydrofuran (THF) | |

EXAMPLE 18

An ISFET sensor was fabricated as in Example 17 except for the fact that N-methyl pyrrole was used as the electrolyte in place of pyrrole.

EXAMPLE 19

An ISFET sensor was fabricated as in Example 17 except for the fact that a sapphire substrate was used as the MOSFET substrate.

EXAMPLE 20

An ISFET sensor was fabricated as in Example 17 except for the fact that the ISFET was of the isolated gate-type shown in FIG. 10.

The characteristics of the hydrogen ion ISFET sensors fabricated in Examples 17-20 were investigated as in Experiment 1a. As the standard solution, use was made of a 0.001-0.2M phosphate buffer solution. Measurement was conducted at a pH of 1.0-12.0 (25° C.). The plot of Vout against hydrogen ion exhibited good linearity over the range 3.0-11.0 for all of the Examples. The slope of the straight line was −59 mV/pH for Example 17, −57 mV/pH for Example 18, 59 mV/pH for Example 19, and 58 mV/pH for Example 20. Values close to theoretical were obtained for all of the Examples. The 95% speed of response was within 5-10 sec, which is very rapid.

Similar results were obtained not only with the hydrogen ion ISFET sensor but also with the potassium ion ISFET sensor, sodium ion ISFET sensor, chlorine ion ISFET sensor, calcium ion ISFET sensor and hydrogencarbonate ion ISFET sensor.

The influence of the amount of oxygen in solution on electromotive force was investigated for the hydrogen ion ISFET sensors in Examples 17-20. Though a change in electromotive force was measured between $PO_2$ 0 mmHg and 600 mmHg by blowing in nigrogen gas, air and the like, the value was less than 0.5 mV in all cases, thus confirming that the sensors were not influenced by oxygen. Similar results were obtained for the potassium ion ISFET sensor, sodium ion ISFET sensor, chlorine ion ISFET sensor, calcium ion ISFET sensor and hydrogencarbonate ion ISFET sensor.

EXAMPLE 21

An ISFET electrode was fabricated by depositing a hydrogen ion-sensitive layer on the gate isolating membrane of a MOSFET by a method which will now be described.

(i) MOSFET

To fabricate the MOSFET on which the hydrogen ion-sensitive layer is deposited, use was made of a FET of needle-like structure. The FET was formed by providing an Si-SiO$_2$ gate isolating membrane on a p-type wafer.

(ii) Hydrogen ion-sensitive layer deposition

A neutral carrier membrane having a composition given herein and containing tri-n-dodecyl amine was deposited on the SiO$_2$ gate isolating membrane of the MOSFET. The tri-n-dodecyl amine (manufactured by Tokyo Kasei) used was distilled twice under a reduced pressure of 5 mmHg with the temperature maintained at 220°-220° C. by an oil bath. Dioctyl sebacate (Tokyo Kasei) and potassium tetrakis-p-chlorophenyl borate (K-TCPB, manufactured by Wako Junyaku) were used in the form available on the market. Polyvinyl chloride (PVC) having an average number of 100 macromolecules was dissolved in THF and the solution was dropped into methanol to again effect precipitation. The resulting precipitate was used upon being dried.

The neutral carrier membrane, whose composition is given hereinbelow, was formed by placing a THF solution containing the composition on the SiO$_2$ gate isolating membrane and subsequently evaporating the solvent by blow-drying. ISFETs where thus fabricated having hydrogen ion-sensitive layers of thicknesses 0.25 mm, 0.45 mm and 1.0 mm. Membrane thickness was measured by a vernier caliper.

| Neutral carrier membrane composition | |
|---|---|
| tri-n-dodecyl amine | 2.3 wt-% |
| dioctyl sebacate (plasticizer) | 64.8 |
| K-TCPB | 0.5 |
| polyvinyl chloride (PVC) | 32.4 |

EXAMPLE 22

The characteristics of the ISFET obtained in Example 21 were investigated by setting up the cell shown in FIG. 4. A change in the surface potential of the hydrogen ion-sensitive layer was measured by constructing a source follower circuit of gain OdB using the cell and measuring the source voltage (Vout). Note that Vout was measured by a digital multimeter TR6841 (Advantest). A sodium chloride saturated calomel electrode (SSCE) was used as the reference electrode.

A solution for pH measurement was prepared by adding sodium hydroxide or a hydrochloric acid solution dropwise to a 1M sodium chloride aqueous solution to obtain a desired pH, with use being made of a digital pH millivoltmeter (Model 801, manufactured by Olion Research Corp.), a glass electrode and the SSCE. Measurement was made at 28° C. at a constant light intensity in an air saturation state while the measurement solution was stirred by a magnetic stirrer.

FIG. 18 is a view showing Vout plotted against pH where Vout was measured before the MOSFET was provided with the neutral carrier membrane deposit, namely in a state where the SiO$_2$ gate isolating membrane was in direct contact with the measurement solution. FIG. 18 shows that Vout does not have a linear relation with respect to pH and that operation is unstable. Accordingly, the arrangement is not suitable for use as a sensor.

Figure 19:
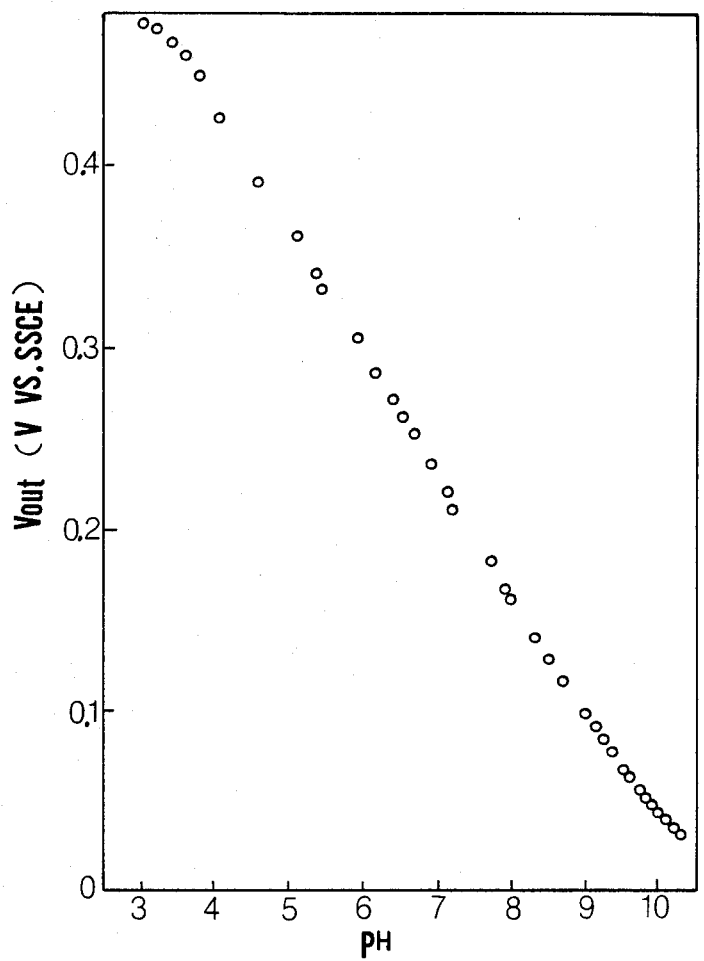
FIG. 19 is a view in which source voltage is plotted against pH when a pH measurement is made using an ISFET electrode (membrane thickness: 0.45 mm) fabricated according to a 21st example of the invention.

By contrast, with the inventive ISFET on which the neutral carrier membrane is deposited (membrane thickness: 0.45 mm), the plot of Vout against pH exhibits excellent linearity and a response having good reproducibility, as depicted in FIG. 19.

Figure 20:
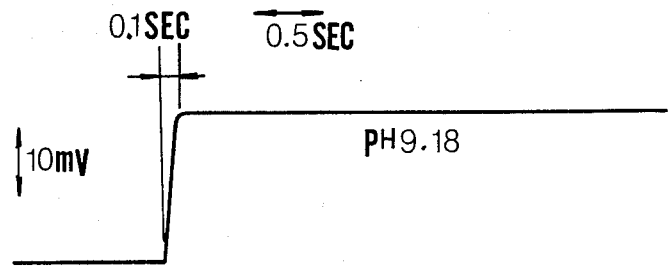
FIGS. 20 and 21 are views illustrating electropotential response when the same ISFET electrode is dipped into a solution of pH 9.18 starting from the open state.
Figure 21:
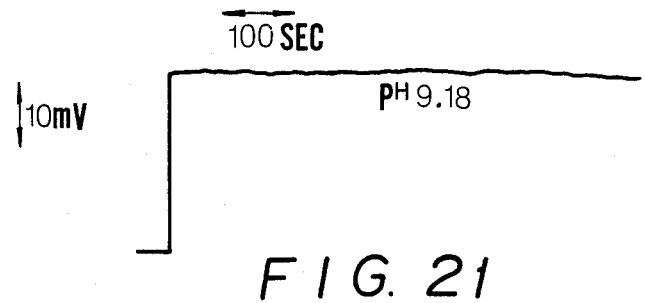

FIG. 20 illustrates an example of results obtained by investigating the speed of response and the stability of Vout with time of the ISFET sensor having the above membrane thickness. The results are for response when the sensor was placed in the 1M NaCl-NaOH aqueous solution (pH 9.18) starting fromthe open state. As illustrated, 95% response time is within 1 sec, which is a very short period of time. FIG. 21 reveals that there is almost no change with the passage of time.

With the ISFET sensor having a neutral carrier membrane thickness of 15 mm, absolutely no dependence of Vout upon pH was found.

EXAMPLES 23-39

Other examples are indicated in Table 2-1-2-4.

As many apparently widely different embodiments of the present invention can be made without departing from the spirit and scope thereofv, it is to be understood that the invention is not limited to the specific embodiments thereof except as defined in the appended claims.

TABLE 2

| | | Examples | | | | | | |
|---|---|---|---|---|---|---|---|---|
| | | 23 | 24 | 25 | 26 | 27 | 28 | 29 |
| electrically conductive radox layer | thickness | 2 μm | 2 μm | 1 μm | 2 μm | 40 μm | 3000Å carbon 2 μm | 3000Å carbon 2 μm |
| | material thickness composition | 0.5 M 2.6-xylenol 0.2 M NaClO$_4$ | 0.5 M 2.6-xylenol 0.2 M NaClO$_4$ | 0.05 M pyrrole 0.2 M NaClO$_4$ | 0.5 M 2.6-xylenol 0.2 M NaClO$_4$ | 0.5 M 2.6-xylenol 0.2 M NaClO$_4$ | 0.5 M 2.6-xylenol 0.2 M NaClO$_4$ | 0.5 M 2.6-xylenol 0.2 M NaClO$_4$ |
| | solvent electrolytic condition | acetonitrile −20° C. | acetonitrile −20° C. | acetonitrile −20° C. | acetonitrile −20° C. | acetonitrile −20° C. | acetonitrile −20° C. | acetonitrile −20° C. |
| ion-sensitive layer | thickness composition (mg/ml) | 400 μm tri(n-dodecyl) amine (10.0) dioctyl sebacate (DOS) (160) potassium tetrakis (p-chlorophenyl) borate (1.5) polyvinyl chloride (PVC) (80) THF (4 ml) | 400 μm 3-hydroxy-N—dodecyl picolin amid (20.0) dioctyl sebacate (DOS) (128) potassium tetrakis (p-chlorophenyl) borate (1.0) polyvinyl chloride (PVC) (68) THF (4 ml) | 300 μm tri(n-dodecyl) amine (10.0) dioctyl sebacate (DOS) (160) potassium tetrakis (p-chlorophenyl) borate (1.5) polyvinyl chloride (PVC) (80) THF (4 ml) | 5 mm tri(n-dodecyl) amine (10.0) dioctyl sebacate (DOS) (160) potassium tetrakis (p-chlorophenyl) borate (1.5) polyvinyl chloride (PVC) (80) THF (4 ml) | 5 mm tri(n-dodecyl) amine (10.0) dioctyl sebacate (DOS) (160) potassium tetrakis (p-chlorophenyl) borate (1.5) polyvinyl chloride (PVC) (80) THF (4 ml) | 400 μm tri(n-dodecyl) amine (10.0) dioctyl sebacate (DOS) (160) potassium tetrakis (p-chlorophenyl) borate (1.5) polyvinyl chloride (PVC) (80) THF (4 ml) | 400 μm 3-hydroxy-N—dodecyle picolin amid (10.0) dioctyl sebacate (DOS) (160) potassium tetrakis (p-chlorophenyl) borate (1.5) polyvinyl chloride (PVC) (80) THF (4 ml) |
| | solvent | | | | | | | |
| selected ion ion selectivity log $K^{pot}_{X^+,Y^+}$ X$^+$...selected ion | | hydrogen ion sodium ion (9.5) potassium ion (9.4) calcium ion (<−10) | hydrogen ion sodium ion (−7.5) potassium ion (−8.2) calcium ion (−7.8) magnesium ion (−7.4) | hydrogen ion sodium ion (9.6) potassium ion (9.4) calcium ion (<−10) | hydrogen ion sodium ion (9.8) potassium ion (9.5) calcium ion (<−10) | hydrogen ion sodium ion (9.8) potassium ion (9.6) calcium ion (<−10) | hydrogen ion sodium ion (−10.2) potassium ion calcium ion (<−10) | hydrogen ion sodium ion (−7.8) potassium ion (−8.2) calcium ion (−8.0) magnesium ion (−7.8) |
| gradient of potencial value vs. pH on a log scale at 37° C. (Nernst's equation) (mV/pH) | | −61.0 | −60.0 | −59.5 | −61.0 | −61.5 | −61.5 | −60.0 |
| response (second) | | 5 | 10 | 10 | 5 | 5 | 2 | 10 |
| change of potencial depending on oxygen (mV) | | ±2 mV | ±2 mV | ±3 mV | ±2 mV | ±2 mV | ±1 mV | ±1 mV |

| | | Examples | | | | | | |
|---|---|---|---|---|---|---|---|---|
| | | 30 | 31 | 32 | 33 | 34 | 35 | 36 |
| electrically conductive radox layer | thickness | 3000Å aurum 1 μm | 3000Å aurum 1 μm | 2 μm | 2 μm | 2 μm | 2 μm | 2 μm |
| | material thickness composition | 0.05 M pyrrole 0.2 M NaClO$_4$ | 0.05 M pyrrole 0.2 M NaClO$_4$ | 0.5 M 2.6-xylenol 0.2 M NaClO$_4$ | 0.5 M 2.6-xylenol 0.2 M NaClO$_4$ | 0.5 M 2.6-xylenol 0.2 M NaClO$_4$ | 0.05 M pyrrole 0.2 M NaClO$_4$ | 0.05 M pyrrole 0.2 M NaClO$_4$ |
| | solvent electrolytic condition | acetonitrile −20° C. | acetonitrile −20° C. | acetonitrile −20° C. | acetonitrile −20° C. | acetonitrile −20° C. | acetonitrile −20° C. | acetonitrile −20° C. |
| ion-sensitive layer | thickness composition (mg/ml) | 400 μm tri(n-dodecyl) amine (10.0) dioctyl sebacate (DOS) (100) potassium tetrakis (p-chlorophenyl) | 400 μm 3-hydroxy-N—dodecyle picolin amid (10.0) dioctyl sebacate (DOS) (160) potassium tetrakis | 400 μm valinomycin (3.2) di(2-ethyl hecyl) sebacate (131.2) polyvinyl chloride (PVC) (65.6) | 500 μm bis[(12-crown-4) methyl] dodecyl malonate (5.98) potassium tetrakis (p-cholorophenyl) borate (1.01) | 500 μm nonactin (25) potassium tetrakis (p-cholorophenyl) borate (5) polyvinyl chloride (PVC) (160) | 400 μm calcium bis[di-(n-octyl phenyl) phosphate] (14.0) di(n-octyl phenyl) phosphate (62.0) polyvinyl chloride | 500 μm N,N′—diheptyl-N,N′—dimethyl-1,4-butan diamide (25) potassium tetrakis (p-cholorophenyl) borate (5) |

TABLE 2-continued

|  | | | | | | | |
|---|---|---|---|---|---|---|---|
| | | borate (1.5) polyvinyl chloride (PVC) (80) | (p-chlorophenyl) borate (1.5) polyvinyl chloride (PVC) (80) | | polyvinyl chloride (PVC) (64.9) di(2-ethyl hexyl) sebacate (129) | dioctyl sebacate (DOS) (320) | (PVC) (62.0) di(2-ethyl hexyl) sebacate (62.0) | polyvinyl chloride (PVC) (300) dioctyl sebacate (DOS) (647) |
| solvent | | THF (4 ml) | THF (4 ml) | THF (4 ml) | THF (4 ml) | THF (4 ml) | THF (4 ml) | THF (4 ml) |
| selected ion ion selectivity $\log K^{Pot}_{X+,Y+}$ X+ . . . selected ion | | hydrogen ion (−4.3) sodium ion (−4.0) potassium ion (−9.5) calcium ion (<−10) | hydrogen ion (−9.5) sodium ion (−9.5) potassium ion (−9.5) calcium ion (−<10) | potassium ion hydrogen ion (−4.3) sodium ion (−4.0) ammonium ion (−2.0) | sodium ion potassium ion (−2.0) ammonium ion (−2.7) | ammonium ion hydrogen ion (−4.0) potassium ion (−1.5) sodium ion (−2.7) calcium ion (−5.1) magnesium ion (−5.4) | calcium ion hydrogen ion (−0.4) potassium ion (−3.3) sodium ion (−3.2) magnesium ion (−3.3) | magnesium ion hydrogen ion (−1.1) potassium ion (−1.5) sodium ion (1.3) calcium ion (1.3) |
| gradient of potencial value vs. pH on a log scale at 37° C. (Nernst's equation) (mV/pH) | | −60.5 | −61.0 | −59.8 | 59.7 | 60.6 | 60.4 | 60.4 |
| response (second) | | 5 | 5 | 1 | 1 | 10 | 10 | 10 |
| change of potencial depending on oxygen (mV) | | ±10 mV | ±10 mV | ±3 mV | ±2 mV | ±2 mV | ±2 mV | ±2 mV |

| | | Examples | | |
|---|---|---|---|---|
| | | 37 | 38 | 39 |
| electrically conductive layer | thickness material | 3000Å carbon | | |
| radox layer | thickness composition | 2 μm 0.5 M 2.6-xylenol 0.2 M NaClO₄ | 2 μm 0.5 M 2.6-xylenol 0.2 M NaClO₄ | 2 μm 0.5 M 2.6-xylenol 0.2 M NaClO₄ |
| | solvent electrolytic condition | acetonitrile −20° C. | acetonitrile −20° C. | acetonitrile −20° C. |
| ion-sensitive layer | thickness composition (mg/ml) | 400 μm valinomycin (3.2) di(2-ethyl hexyl) sebacate (131.2) polyvinyl chloride (PVC) (65.6) | 400 μm tri(n-dodecyl) ammonium chloride (6.6) di(2-ethyl hexyl) sebacate (128.8) polyvinyl chloride (PVC) (64.6) | 400 μm triphenyl tin chloride (11.2) polyvinyl chloride (PVC) (63.0) di(2-ethyl hexyl) sebacate (125.8) |
| | solvent | THF (4 ml) | THF (4 ml) | THF (4 ml) |
| selected ion | | potassium ion | hydrogencarbonate ion | chloride ion |
| ion selectivity $\log K^{Pot}_{X+,Y+}$ X+ . . . selected ion | | hydrogen ion (−4.4) sodium ion (−4.1) ammonium ion (−2.1) | perchloric chloride ion (−2.5) chloride ion (−2.0) | perchloric chloride ion (−2.5) hydrogencarbonate ion (−2.3) |
| gradient of potencial value vs. pH on a log scale at 37° C. (Nernst's equation) (mV/pH) | | 60.0 | −60.7 | −61.2 |
| response (second) | | 1 | 10 | 1 |
| change of potencial depending on oxygen (mV) | | ±1 mV | ±2 mV | ±2 mV |

What we claim is:

1. An ion-sensitive FET sensor comprising:
a MOSFET having a gate portion;
a redox layer containing at least one material capable of undergoing a quinone-hydroquinone type redox reaction covering a surface of an isolating membrane of the gate portion; and
an ion-sensitive layer exhibiting ion selectivity covering a surface of said redox layer, wherein said ion-sensitive layer generates a potential corresponding to a concentration of an ion of interest and said redox layer generates an electric field on the gate portion of the MOSFET corresponding to the potential generated by the ion-sensitive layer.

2. The ion-sensitive FET sensor according to claim 1, further comprising an electrically conductive layer exhibiting electrical conductivity between said surface of said isolating membrane of said gate portion and said redox layer.

3. The ion-sensitive FET sensor according to claim 2, wherein said electrically conductive layer is comprised of multiple conductive layers.

4. The ion-sensitive FET sensor according to claim 1, wherein said redox layer has a thickness of from 0.01 μm to 1.0 mm.

5. The ion-sensitive FET sensor according to claim 1, wherein said ion-sensitive layer has a thickness of from 1 μm to 10 mm.

6. The ion-sensitive FET sensor according to claim 1, wherein said ion-sensitive layer, comprising an organic polymeric membrane containing an ion carrier material, which is a compound expressed by the formula

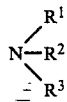

where $R^1$, $R^2$, $R^3$ represent the same or different alkyl groups, among which at least two alkyl groups have a carbon number of 8-18, and is selective to hydrogen ion.

7. The ion-sensitive FET sensor according to claim 1, wherein said ion-sensitive layer, comprising an organic polymeric membrane containing an ion carrier material, which is a compound expressed by the formula

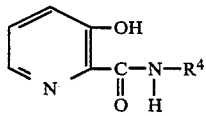

where $R^4$ represents an alkyl group having a carbon number of 8-18, and is selective to hydrogen ion.

8. The ion-sensitive FET sensor according to claim 1, wherein said ion-sensitive layer, comprising an organic polymeric membrane containing an ion carrier material, which is selected from the group consisting of valinomycin, nonactin, monactin, crown ether compounds comprising dicyclohexyl-18-crown-6, naphtho-15-crown-5, bis(15-crown-5), and is selective to potassium ion.

9. The ion-sensitive FET sensor according to claim 1, wherein said ion-sensitive layer, comprising an organic polymeric membrane containing an ion carrier material, which is selected from the group consisting of aromatic amides or diamides, aliphatic amides or diamides, and crown compounds, and is selective to sodium ion.

10. The ion-sensitive FET sensor according to claim 1, wherein said ion-sensitive layer, comprising an organic polymeric membrane containing an ion carrier material, which is selected from the group of the quaternary ammonium salts expressed by the formula

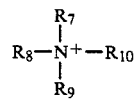

and is selective to chlorine ion wherein $R_7$, $R_8$ and $R_9$ represent the same or different alkyl groups $C_8$–$C_{18}$ and $R_{10}$ represents hydrogen or a $C_1$ to $C_8$ alkyl group.

11. The ion-sensitive FET sensor according to claim 1, wherein said ion-sensitive layer, comprising an organic polymeric membrane containing an ion carrier material, triphenyl tin chloride expressed by the formula

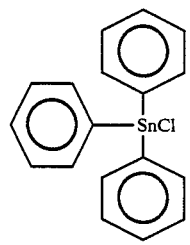

is selective to chlorine ion.

12. The ion-sensitive FET sensor according to claim 1, wherein said ion-sensitive layer, comprising an organic polymeric membrane containing an ion carrier material, which is selected from the group consisting of bis(di-(octylphenyl)phosphate), (−)-(R,R)-N,N'-bis(11-ethoxy carbonyl)undecyl)-N,N',4,5-tetramethyl-3,6-dioxaoctane-diamide and calcium bis(di(n-decyl)phosphate), and is selective to calcium ion.

13. The ion-sensitive FET sensor according to claim 1, wherein said ion-sensitive layer, comprising an organic polymeric membrane containing an ion carrier material, which is selected from the group of quaternary ammonium salts expressed by the formula

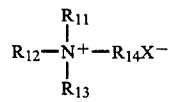

and is selective to hydrogencarbonate ion wherein $R_{11}$, $R_{12}$ and $R_{13}$ represent the same or different $C_8$ to $C_{18}$ alkyl groups and $R_{14}$ represents a hydrogen or a $C_1$ to $C_4$ alkyl group and X represents Cl, Br or OH.

14. The ion-sensitive FET sensor according to claim 1, wherein said ion-sensitive layer, comprising an organic polymeric membrane containing an ion carrier material, which is selected from the group of tertiary amine compounds expressed by the formula

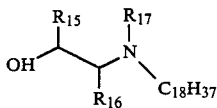

and is selective to hydrogencarbonate ion wherein $R_{15}$ represents a phenyl group, hydrogen or a methyl group, $R_{16}$ represents hydrogen, or methyl and $R_{17}$ represents methyl or octadecyl.

15. The ion-sensitive FET sensor according to claim 1, wherein said ion-sensitive layer, comprising an organic polymeric membrane containing an ion carrier material, which is selected from the group of tertiary amine compounds expressed by the formula

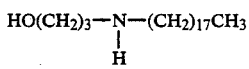

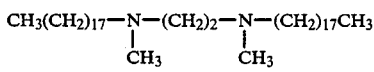

selects hydrogencarbonate ion.

16. The ion-sensitive FET sensor according to claim 1, wherein said ion-sensitive layer, comprising an organic polymeric membrane containing a ion carrier material nonactin or monactin containing nonalkene, and is selective to ammonium ion.

17. The ion-sensitive FET sensor according to claim 1, wherein said ion-sensitive layer, comprising an organic polymeric membrane containing an ion carrier material, N,N'-diheptyl-N,N'-dimethyl-1,4-butane diamide, and is selective to magnesium ion.

18. An ion-sensitive FET sensor comprising:
a MOSFET having a gate portion;
a redox layer containing at least one material capable of undergoing an amine-quinoid type redox reaction covering a surface of an isolating membrane of the gate portion; and
an ion-sensitive layer exhibiting ion selectivity covering the surface of said redox layer, wherein said ion-sensitive layer generates a potential corresponding to a concentration of an ion of interest and said redox layer generates an electric field on the gate portion of the MOSFET corresponding to the potential generated by the ion-sensitive layer.

19. The ion-sensitive FET sensor according to claim 18, further comprising an electrically conductive layer exhibiting electrical conductivity between said surface of said isolating membrane of said gate portion and said redox layer.

20. The ion-sensitive FET sensor according to claim 19, wherein said electrically conductive layer is comprised of multiple conductive layers.

21. The ion-sensitive FET sensor according to claim 18, wherein said redox layer has a thickness of from 0.01 μm to 1.0 mm.

22. The ion-sensitive FET sensor according to claim 18, wherein said electrically conductive layer is selected from the group consisting of carbon, metals and metallic oxides.

23. The ion-sensitive FET sensor according to claim 22, wherein said electrically conductive layer comprises multiple layers.

24. The ion-sensitive FET sensor according to claim 22, wherein said electrically conductive layer has a thickness of from 0.01 μm to 1 μm.

25. The ion-sensitive FET sensor according to claim 18, wherein said ion-sensitive layer has a thickness of from 1 μm to 10 mm.

26. The ion-sensitive FET sensor according to claim 18, wherein said ion-sensitive layer, comprising an organic polymeric membrane containing an ion carrier material, which is a compound expressed by the formula

where $R^1$, $R^2$, $R^3$ represent the same or different alkyl groups, among which at least two alkyl groups have a carbon number of 8-18, and is selective to hydrogen ion.

27. The ion-sensitive FET sensor according to claim 18, wherein said ion-sensitive layer, comprising an organic polymeric membrane containing an ion carrier material, which is a compound expressed by the formula

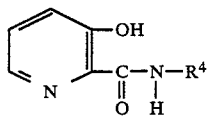

where $R^4$ represents an alkyl group having a carbon number of 8-18, and is selective to hydrogen ion.

28. The ion-sensitive FET sensor according to claim 18, wherein said ion-sensitive layer, comprising an organic polymeric membrane containing an ion carrier material, which is selected from the group consisting of aromatic amides or diamides, aliphatic amides or diamides, and crown compounds, and is selective to sodium ion.

29. The ion-sensitive FET sensor according to claim 18, wherein said ion-sensitive layer, comprising an organic polymeric membrane containing an ion carrier material, which is selected from the group of quaternary ammonium salts expressed by the formula

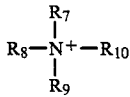

and is selected to chlorine ion wherein $R_7$, $R_8$ and $R_9$ represent the same or different $C_8$ to $C_{18}$ alkyl groups and $R_{10}$ represents a hydrogen or a $C_1$ to $C_8$ alkyl group.

30. The ion-sensitive FET sensor according to claim 18, wherein said ion-sensitive layer, comprising an organic polymeric membrane containing an ion carrier material triphenyl tin chloride expressed by the formula

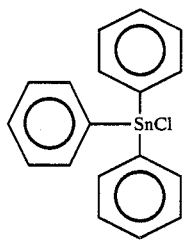

and is selective to chlorine ion.

31. The ion-sensitive FET sensor according to claim 18, wherein said ion-sensitive layer, comprising an organic polymeric membrane containing an ion carrier material, which is selected from the group consisting of bis(di-(octylphenyl)phosphate), (—)-(R,R)-N,N'-bis(11-ethoxy carbonyl)undecyl)-N,N',4,5-tetramethyl-3,6-dioxaoctane-diamide and calcium bis(di(n-decyl)phosphate), and is selective to calcium ion.

32. The ion-sensitive FET sensor according to claim 18, wherein said ion-sensitive layer, comprising an organic polymeric membrane containing an ion carrier material, which is selected from the group of quaternary ammonium salts expressed by the formula

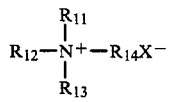

and is selective to hydrogencarbonate ion wherein $R_{11}$, $R_{12}$ and $R_{13}$ represent the same or different $C_8$ to $C_{18}$ alkyl groups and $R_{14}$ represents a hydrogen or a $C_1$ to $C_4$ alkyl group and X represents Cl, Br or OH.

33. The ion-sensitive FET sensor according to claim 18, wherein said ion-sensitive layer, comprising an organic polymeric membrane containing an ion carrier material, which is selected from the group or tertiary amine compounds expressed by the formula

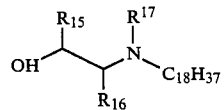

and is selective to hydrogencarbonate ion wherein $R_{15}$ represents a phenyl group, hydrogen or a methyl group, $R_{16}$ represents hydrogen, or methyl and $R_{17}$ represents methyl or octadecyl.

34. The ion-sensitive FET sensor according to claim 18, wherein said ion-sensitive layer, comprising an organic polymeric membrane containing an ion carrier material, which is selected from the group of tertiary amine compounds expressed by the formula

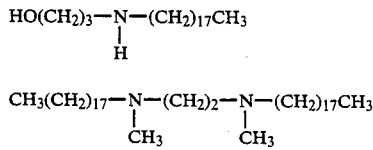

and is selective to hydrogencarbonate ion.

35. The ion-sensitive FET sensor according to claim 18, wherein said ion-sensitive layer, comprising an organic polymeric membrane containing an ion carrier material, nonactin or monactin containing nonactin, and is selective to ammonium ion.

36. The ion-sensitive FET sensor according to claim 18, wherein said ion-sensitive layer, comprising an organic polymeric membrane containing an ion carrier material, N,N'-diheptyl-N,N'-dimethyl-1,4-butane diamide, and is selective to magnesium ion.

37. The ion-sensitive FET sensor according to claim 18, wherein said ion-sensitive layer is selective to potassium ion, and comprises an organic polymeric membrane containing an ion carrier material selected from the group consisting of valinomycin, nonactin, monactin and crown ether compounds.

38. The ion-sensitive FET sensor according to Claim 37, wherein crown ether compounds are dicyclohexyl-18-crown-6, naphtho-15-crown-5 and bis(15-crown-5).

39. An ion-sensitive FET sensor comprising:
a MOSFET having a gate portion;
a redox layer containing at least one member selected from the group consisting of poly(pyrrole) and poly(thionylene) covering a surface of an isolating membrane of the gate portion; and
an ion-sensitive layer exhibiting ion selectivity covering a surface of said redox layer, wherein said ion-sensitive layer generates a potential corresponding to a concentration of an ion of interest and said redox layer generates an electric field on the gate portion of the MOSFET corresponding to the potential generated by the ion-sensitive layer.

40. The ion-sensitive FET sensor according to claim 39, further comprising an electrically conductive layer exhibiting electrical conductivity between said surface of said isolating membrane of said gate portion and said redox layer.

41. The ion-sensitive FET sensor according to claim 40, wherein said electrically conductive layer is comprised of multiple conductive layers.

42. The ion-sensitive FET sensor according to claim 39, wherein said redox layer has a thickness of from 0.01 μm to 1.0 mm.

43. The ion-sensitive FET sensor according to claim 39, wherein said electrically conductive layer is selected from the group consisting of carbon, metals and metallic oxides.

44. The ion-sensitive FET sensor according to claim 39, wherein said electrically conductive layer has a thickness of from 0.01 μm to 1 μm.

45. The ion-sensitive FET sensor according to claim 39, wherein one of said multiple layers is selected from the group consisting of nickel, chromium and gold, wherein said one layer covers the insulating membrane.

46. The ion-sensitive FET sensor according to claim 39, wherein said ion-sensitive layer has a thickness of from 1 μm to 10 mm.

47. The ion-sensitive FET sensor according to claim 39, wherein said ion-sensitive layer, comprising an organic polymeric membrane containing an ion carrier material, which is a compound expressed by the formula

where $R^1$, $R^2$, $R^3$ represent the same or different alkyl groups, among which at least two alkyl groups have a carbon number of 8-18, and is selective to hydrogen ion.

48. The ion-sensitive FET sensor according to claim 39, wherein said ion-sensitive layer, comprising an organic polymeric membrane containing an ion carrier material, which is a compound expressed by the formula

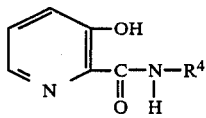

where $R^4$ represents an alkyl group having a carbon number of 8-18, and is selective to hydrogen ion.

49. The ion-sensitive FET sensor according to claim 39, wherein said ion-sensitive layer, comprising an organic polymeric membrane containing an ion carrier material, which is selected from the group consisting of aromatic amides or diamides, aliphatic amides or diamides, and crown compounds, and is selective to sodium ion.

50. The ion-sensitive FET sensor according to claim 39, wherein said ion-sensitive layer, comprising an organic polymeric membrane containing an ion carrier material, which is selected from the group of quaternary ammonium salts expressed by the formula

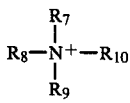

and is selective to chlorine ion wherein $R_7$, $R_8$ and $R_9$ represent the same or different $C_8$ to $C_{18}$ alkyl groups and $R_{10}$ represents a hydrogen or a $C_1$ to $C_8$ alkyl group.

51. The ion-sensitive FET sensor according to claim 39, wherein said ion-sensitive layer, comprising an organic polymeric membrane containing an ion carrier material, triphenyl tin chloride expressed by the formula

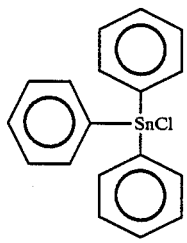

and is selective to chlorine ion.

52. The ion-sensitive FET sensor according to claim 39, wherein said ion-sensitive layer, comprising an organic polymeric membrane containing an ion carrier material, which is selected from the group consisting of bis(di-(octylphenyl)phosphate, (31 )-(R,R)-N,N'-bis(11-ethoxy carbonyl) undecyl(-N,N',4,5-tetramethyl-3,6-dioxaoctane-diamide and calcium bis(di(n-decyl) phosphate), and is selective to calcium ion.

53. The ion-sensitive FET sensor according to claim 39, wherein said ion-sensitive layer, comprising an organic polymeric membrane containing an ion carrier material, which is selected from the group of quanternary ammonium salts expressed by the formula

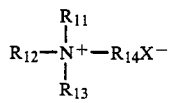

and is selective to hydrogencarbonate ion wherein $R_{11}$, $R_{12}$ and $R_{13}$ represent the same or different $C_8$ to $C_{18}$ alkyl groups and $R_{14}$ represents a hydrogen or a $C_1$ to $C_4$ alkyl group and X represents Cl, Br or OH.

54. The ion-sensitive FET sensor according to claim 39, wherein said ion-sensitive layer, comprising an organic polymeric membrane containing an ion carrier material, which is selected from the group of tertiary amine compounds expressed by the formula

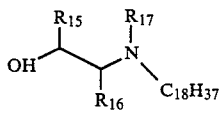

and is selective to hydrogencarbonate ion wherein $R_{15}$ represents a phenyl group, hydrogen or a methyl group, $R_{16}$ represents hydrogen, or methyl and $R_{17}$ represents methyl or octadecyl.

55. The ion-sensitive FET sensor according to claim 39, wherein said ion-sensitive layer, comprising an organic polymeric membrane containing an ion carrier material, which is selected from the group of tertiary amine compounds expressed by the formula

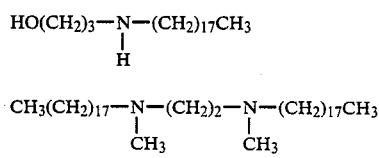

and is selective to hydrogencarbonate ion.

56. The ion-sensitive FET sensor according to claim 39, wherein said ion-sensitive layer, comprising an organic polymeric membrane containing an ion carrier material, nonactin or monactin containing nonactin, and is, selective to ammonium ion.

57. The ion-sensitive FET sensor according to claim 39, wherein said ion-sensitive layer, comprising an organic polymeric membrane containing an ion carrier material, N,N'-diheptyl-N,N'-dimethyl-1,4-butane diamide, and is selective to magnesium ion.

58. The ion-sensitive FET sensor according to claim 39, wherein said ion-sensitive layer is selective to potassium ion, and comprises an organic polymeric membrane containing an ion carrier material selected from the group consisting of valinomycin, nonactin, monactin and crown ether compounds.

59. The ion-sensitive FET sensor according to claim 58, wherein crown ether compounds are dicyclohexyl-18-crown-6, naphtho-15-crown-5 and bis(15-crown-5).

* * * * *